(12) United States Patent
Kappel et al.

(10) Patent No.: US 10,525,100 B2
(45) Date of Patent: Jan. 7, 2020

(54) ATF5 PEPTIDE VARIANTS AND USES THEREOF

(71) Applicant: Sapience Therapeutics, Inc., Harrison, NY (US)

(72) Inventors: Barry Jay Kappel, Pelham, NY (US); Gene Merutka, Phoenixville, PA (US); Jimmy Andrew Rotolo, Port Washington, NY (US)

(73) Assignee: Sapience Therapeutics, Inc., Harrison, NY (US)

( * ) Notice: Subject to any disclaimer, the term of this patent is extended or adjusted under 35 U.S.C. 154(b) by 0 days.

(21) Appl. No.: 16/239,217

(22) Filed: Jan. 3, 2019

(65) Prior Publication Data
US 2019/0201483 A1    Jul. 4, 2019

Related U.S. Application Data

(60) Provisional application No. 62/613,083, filed on Jan. 3, 2018.

(51) Int. Cl.
| *A61K 38/17* | (2006.01) |
| *C07K 14/47* | (2006.01) |
| *A61P 35/00* | (2006.01) |
| *C12N 15/85* | (2006.01) |

(52) U.S. Cl.
CPC .............. *A61K 38/17* (2013.01); *A61P 35/00* (2018.01); *C07K 14/47* (2013.01); *C07K 14/4705* (2013.01); *C12N 15/85* (2013.01)

(58) Field of Classification Search
CPC ......... A61K 38/17; C07K 14/47; A61P 35/00; C12N 15/85
USPC ..... 514/19.2, 1.1, 21.3, 21.4, 21.6; 530/300, 530/324, 326
See application file for complete search history.

(56) References Cited

U.S. PATENT DOCUMENTS

| 5,942,433 A | 8/1999 | Vinson et al. |
| 5,955,593 A | 9/1999 | Korsmeyer |
| 5,998,583 A | 12/1999 | Korsmeyer |
| 6,221,355 B1 | 4/2001 | Dowdy |
| 6,261,569 B1 | 7/2001 | Comis et al. |
| 6,303,576 B1 | 10/2001 | Blaschuk et al. |
| 6,361,968 B1 | 3/2002 | Vinson et al. |
| 6,468,754 B1 | 10/2002 | Greene et al. |
| 6,485,977 B1 | 11/2002 | Collmer et al. |
| 6,551,795 B1 * | 4/2003 | Rubenfield ............ C07K 14/21 435/253.3 |
| 7,611,893 B2 * | 11/2009 | Mascarenhas ........... B82Y 5/00 435/320.1 |
| 7,888,326 B2 | 2/2011 | Greene et al. |
| 8,183,339 B1 | 5/2012 | Bonny |
| 8,957,026 B2 | 2/2015 | Verdine et al. |
| 9,758,555 B1 | 9/2017 | Greene et al. |
| 10,316,077 B2 | 6/2019 | Kappel et al. |
| 2002/0160002 A1 | 10/2002 | Gelman |
| 2007/0092495 A1 | 4/2007 | Greene et al. |
| 2012/0093919 A1 | 4/2012 | Bertino et al. |
| 2015/0094271 A1 | 4/2015 | Lee et al. |
| 2016/0008480 A1 | 1/2016 | Lee et al. |

FOREIGN PATENT DOCUMENTS

| WO | WO 2008/072777 | 6/2008 |
| WO | WO 2008/151037 | 12/2008 |
| WO | WO 2011/097513 | 8/2011 |
| WO | WO 2013/013105 | 1/2013 |
| WO | WO 2017/062518 | 4/2017 |

OTHER PUBLICATIONS

Acharya et al., Experimental identification of homodimerizing B-ZIP families in *Homo sapiens*, J. Struct. Biol. 155:130-139, 2006.
Angelastro et al., Regulated Expression of ATF5 is Required for the Progression of Neural Progenitor Cells to Neurons, J. Neurosci. 23:4590-4600, 2003.
Angelastro et al., Downregulation of ATF 5 is Required for Differentiation of Neural Progenitor Cells into Astrocytes, J. Neurosci. 25:3889-3899, 2005.
Angelastro et al., Selective destruction of glioblastoma cells by interference with the activity or expression of ATF5, Oncogene 25:907-916, 2006.
Araghi et al., Designing helical peptide inhibitors of protein-protein interactions, Curr. Opin. Struct. Biol. 39:27-38, 2016.
Arias et al., Regulated ATF5 loss-of-function in adult mice blocks formation and causes regression/eradication of gliomas, Oncogene 31:739-751, 2012.
Cates et al., Regression/Eradication of gliomas in mice by a systematicallly-deliverable ATF5 dominant-negative peptide, Oncotarget 11:12718-12730, 2016.
Ciaccio et al., High-yield expression in *E. coli* and refolding of the bZIP domain of activating transcription factor 5, Protein Expr. Purif. 62:235-243, 2008.
Ciaccio et al., Influence of the Valine Zipper Region on the Structure and Aggregation of the Basic Leucine Zipper (bZIP) Domain of ATF5, Mol. Pharm. 9:3190-3199, 2012.
Dluzen et al., BCL-2 is a Downstream Target of ATF5 That Mediates the Prosurvival Function of ATF5 in a Cell Type-dependent Manner, J. Biol. Chem. 286:7705-7713, 2011.
Greene et al., The transcription factor ATF5: role in neurodevelopment and neural tumors, J. Neurochem. 108:11-22, 2009.
Heitz et al., Twenty years of cell-penetrating peptides: from molecular mechanisms to therapeutics, Brit. J. Pharm. 157:195-206, 2009.
Herve et al., CNS Delivery Via Adsorptive Transcytosis, AAPS J. 10:455-472 , 2008.

(Continued)

*Primary Examiner* — Julie Ha
(74) *Attorney, Agent, or Firm* — Grimes & Yvon LLP

(57) ABSTRACT

Provided are activating transcription factor 5 (ATF5) peptides having a truncated ATF5 leucine zipper region and, optionally, a cell-penetrating region, compositions comprising the ATF5 peptides, and methods of inhibiting proliferation of and promoting cytotoxicity in a neoplastic cell using the ATF5 peptides.

9 Claims, 26 Drawing Sheets

Specification includes a Sequence Listing.

(56) References Cited

OTHER PUBLICATIONS

Karpel-Massler et al., A Synthetic Cell-Penetrating Dominant-Negative ATF5 Peptide Exerts Anticancer Activity . . . , Clin. Cancer Res. doi: 10.1158/1078-0432.CCR-15-2827, 2016.
Krautwald et al., Inhibition of regulated cell death by cell-penetrating peptides, Cell. Mol. Life Sci. 73:2269-2284, 2016.
Krylov et al., Extending dimerization interfaces: the bZIP basic region can form a colied coil, EMBO J. 14:5329-5337, 1995.
Krylov et al., A general method to design dominant negatives to B-HLHZip proteins that abolish DNA binding, Proc. Natl. Acad. Sci., USA 94:12274-12279, 1997.
Lee et al., Reciprocal Actions of ATF5 and Shh in Proliferation of Cerebellar Granule Neuron Progenitor Cells, Dev. Neurobiol. 72:789-804, 2012.
Li, et al., Identification of a Novel DNA Binding Site and a Transcriptional Target for ATF5 in C6 Glioma and MCF-7 Breast Cancer Cells, Mol. Cancer Res. 7:933-943, 2009.
Liu et al., Nucleophosmin (NPM1/B23) Interacts with Activating Transcription Factor 5 (ATF5) Protein . . . , J. Biol. Chem. 287:19599-19609, 2012.
Mason et al., ATF5 regulates the proliferation and differentiation of oligodendrocytes, Mol. Cell. Neurosci. 29:372-380, 2005.
Moll et al., Attractive Interhelical Electrostatic Interactions in the Praline- and Acidic-Rich Region (PAR) Leucine Zipper Subfamily . . . , J. Biol. Chem. 275:34826-34832, 2000.
Monaco et al., The transcription factor ATF5 is widely expressed in carcinomas, and interference with its function selectively kills . . . , Int. J. Cancer 120:1883-1890, 2007.
Munyendo et al., Cell Penetrating Peptides in the Delivery of Biophharmaceuticals, Biomolecules 2:187-202, 2012.
Olive et al., A Dominant Negative to Activation Protein-1 (AP1) That Abolishes DNA Binding and Inhibits Oncogenesis, J. Biol. Chem. 272:18586-18594, 1997.
Schmidt et al., Identification of Short Hydrophobic Cell-Penetrating Peptides for Cytosolic Peptide Delivery by Rational Design, Bioconjugate Chem. 28:382-389, 2017.
Sears et al., The transcription factor ATF5: role in cellular differentiatio, stress responses, and cancer, Oncotarget 8:84595-84609, 2017.
UniProtKB—Q9Y2D1 (ATF5_Human), 2010.
Vinson et al., Dimerization specificity of the leucine zipper-containing bZIP motif on DNA binding: prediction and rational design, Genes & Devel. 7:1047-1058, 1993.
Zou et al., Cell-Penetrating Peptide-Mediating Therapeutic Molecule Delivery into the Central Nervous System, Curr. Neuropharmacol. 11:197-208, 2013.
Abe et al., N-terminal Hydrophobic Amino Acids of . . . (ATF5) Protein Confer . . . (IL-1β)-induced Stabilization, J. Biol. Chem. 289:3888-3900, 2014.
Chorev, The Partial Retro-Inverso Modification: A Road Traveled Together, Biopolymers (Peptide Sci.) 80:67-84, 2005.

* cited by examiner

LEQRAEELARENEELLEKEAEELEQENAELEGECQGLEARNRELRERAESVEREI
QYVKDLLIEVYKARSQRTRSA (SEQ ID NO: 1)

Figure 1A

*RQIKIWFQNRRMKWKK*LEQRAEELARENEELLEKEAEELEQENAELEGECQGLEAR
NRELRERAESV
(SEQ ID NO: 2)

Figure 1B

*RQIKIWFQNRRMKWKK*LEGECQGLEARNRELKERAESV
(SEQ ID NO: 3)

Figure 1C

SEQUENCE LISTING

```
<160> NUMBER OF SEQ ID NOS: 87

<210> SEQ ID NO 1
<211> LENGTH: 76
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1
```

```
Leu Glu Gln Arg Ala Glu Glu Leu Ala Arg Glu Asn Glu Glu Leu Leu
1               5                   10                  15

Glu Lys Glu Ala Glu Glu Leu Glu Gln Glu Asn Ala Glu Leu Glu Gly
                20                  25                  30

Glu Cys Gln Gly Leu Glu Ala Arg Asn Arg Glu Leu Arg Glu Arg Ala
                35                  40                  45

Glu Ser Val Glu Arg Glu Ile Gln Tyr Val Lys Asp Leu Leu Ile Glu
            50                  55                  60

Val Tyr Lys Ala Arg Ser Gln Arg Thr Arg Ser Ala
65              70                  75

<210> SEQ ID NO 2
<211> LENGTH: 67
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Arg Gln Ile Lys Ile Trp Phe Gln Asn Arg Arg Met Lys Trp Lys Lys
1               5                   10                  15

Leu Glu Gln Arg Ala Glu Glu Leu Ala Arg Glu Asn Glu Glu Leu Leu
                20                  25                  30

Glu Lys Glu Ala Glu Glu Leu Glu Gln Glu Asn Ala Glu Leu Glu Gly
                35                  40                  45

Glu Cys Gln Gly Leu Glu Ala Arg Asn Arg Glu Leu Arg Glu Arg Ala
            50                  55                  60

Glu Ser Val
65

<210> SEQ ID NO 3
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Arg Gln Ile Lys Ile Trp Phe Gln Asn Arg Arg Met Lys Trp Lys Lys
1               5                   10                  15

Leu Glu Gly Glu Cys Gln Gly Leu Glu Ala Arg Asn Arg Glu Leu Lys
                20                  25                  30

Glu Arg Ala Glu Ser Val
            35

<210> SEQ ID NO 4
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Arg Gln Ile Lys Ile Trp Phe Gln Asn Arg Arg Met Lys Trp Lys Lys
1               5                   10                  15

Leu Glu Gly Glu Gly Gln Gly Leu Glu Ala Arg Asn Arg Glu Leu Lys
                20                  25                  30
```

Glu Arg Ala Glu Ser Val
        35

<210> SEQ ID NO 5
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Arg Gln Ile Lys Ile Trp Phe Gln Asn Arg Arg Met Lys Trp Lys Lys
1               5                   10                  15

Leu Glu Gly Glu Ala Gln Gly Leu Glu Ala Arg Asn Arg Glu Leu Lys
            20                  25                  30

Glu Arg Ala Glu Ser Val
        35

<210> SEQ ID NO 6
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Arg Gln Ile Lys Ile Trp Phe Gln Asn Arg Arg Met Lys Trp Lys Lys
1               5                   10                  15

Leu Glu Gly Glu Cys Gln Gly Leu Glu Ala Arg Asn Arg Glu Leu Lys
            20                  25                  30

Glu Arg Ala Glu Ala Val
        35

<210> SEQ ID NO 7
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Arg Gln Ile Lys Ile Trp Phe Gln Asn Arg Arg Met Lys Trp Lys Lys
1               5                   10                  15

Leu Glu Gly Glu Cys Gln Gly Leu Glu Ala Arg Leu Arg Glu Leu Lys
            20                  25                  30

Glu Arg Ala Glu Ser Val
        35

<210> SEQ ID NO 8
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Arg Gln Ile Lys Ile Trp Phe Gln Asn Arg Arg Met Lys Trp Lys Lys
1               5                   10                  15

Leu Glu Gly Glu Cys Ala Gly Leu Glu Ala Arg Asn Arg Glu Leu Lys
            20                  25                  30

Glu Arg Ala Glu Ser Val
        35

<210> SEQ ID NO 9
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Arg Gln Ile Lys Ile Trp Phe Gln Asn Arg Arg Met Lys Trp Lys Lys
1               5                   10                  15

Leu Glu Gly Arg Cys Gln Gly Leu Arg Ala Glu Asn Arg Glu Leu Glu
            20                  25                  30

Glu Arg Ala Glu Ser Val
        35

<210> SEQ ID NO 10
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Arg Gln Ile Lys Ile Trp Phe Gln Asn Arg Arg Met Lys Trp Lys Lys
1               5                   10                  15

Leu Glu Gly Arg Cys Gln Gly Leu Arg Ala Glu Leu Arg Glu Leu Glu
            20                  25                  30

Glu Arg Ala Glu Ala Val
        35

<210> SEQ ID NO 11
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Arg Gln Ile Lys Ile Trp Phe Gln Asn Arg Arg Met Lys Trp Lys Lys
1               5                   10                  15

Leu Glu Gly Arg Ala Gln Gly Leu Arg Ala Glu Leu Arg Glu Leu Glu
            20                  25                  30

Glu Arg Ala Glu Ala Val
        35

<210> SEQ ID NO 12
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Arg Gln Ile Lys Ile Trp Phe Gln Asn Arg Arg Met Lys Trp Lys Lys
1               5                   10                  15

Leu Glu Gly Arg Ala Ala Gly Leu Arg Ala Glu Leu Arg Glu Leu Glu

```
                20                  25                  30

Glu Arg Ala Glu Ala Val
            35

<210> SEQ ID NO 13
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(38)
<223> OTHER INFORMATION: D-amino acid

<400> SEQUENCE: 13

Val Ala Glu Ala Arg Glu Glu Leu Glu Arg Leu Glu Ala Arg Leu Gly
1               5                   10                  15

Gln Ala Arg Gly Glu Leu Lys Lys Trp Lys Met Arg Arg Asn Gln Phe
            20                  25                  30

Trp Ile Lys Ile Gln Arg
            35

<210> SEQ ID NO 14
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(38)
<223> OTHER INFORMATION: D-amino acid

<400> SEQUENCE: 14

Val Ala Glu Ala Arg Glu Glu Leu Glu Arg Leu Glu Ala Arg Leu Gly
1               5                   10                  15

Gln Ala Arg Gly Glu Leu Lys Lys Trp Lys Met Arg Arg Asn Gln Phe
            20                  25                  30

Trp Leu Lys Leu Gln Arg
            35

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Phe Lys Lys Phe Arg Lys Phe
1               5

<210> SEQ ID NO 16
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Leu Ile Arg Leu Trp Ser His Leu Ile His Ile Trp Phe Gln Asn Arg
```

```
1               5                   10                  15
Arg Leu Lys Trp Lys Lys Lys
            20

<210> SEQ ID NO 17
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Ala Leu Phe Leu Gly Trp Leu Gly Ala Ala Gly Ser Thr Met Gly
1               5                   10                  15

Ala Trp Ser Gln Pro Lys Lys Lys Arg Lys Val
            20                  25

<210> SEQ ID NO 18
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ala Ala Val Ala Leu Leu Pro Ala Val Leu Leu Ala Leu Leu Ala Pro
1               5                   10                  15

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Glu Arg Lys Lys Arg Arg Arg Glu
1               5

<210> SEQ ID NO 20
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Leu Gly Thr Tyr Thr Gln Asp Phe Asn Lys Thr Phe Pro Gln Thr Ala
1               5                   10                  15

Ile Gly Val Gly Ala Pro
            20

<210> SEQ ID NO 21
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Lys Leu Ala Leu Lys Leu Ala Leu Lys Ala Leu Lys Ala Ala Leu Lys
```

-continued

```
1               5                   10                  15

Leu Ala

<210> SEQ ID NO 22
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gly Leu Ala Phe Leu Gly Phe Leu Gly Ala Ala Gly Ser Thr Met Gly
1               5                   10                  15

Ala Trp Ser Gln Pro Lys Lys Lys Arg Lys Val
            20                  25

<210> SEQ ID NO 23
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Val Gln Arg Lys Arg Gln Lys Leu Met Pro
1               5                   10

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gly Arg Lys Arg Lys Lys Arg Thr
1               5

<210> SEQ ID NO 25
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Arg Gln Ile Lys Ile Trp Phe Gln Asn Arg Arg Met Lys Trp Lys Lys
1               5                   10                  15

<210> SEQ ID NO 26
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Arg Gln Leu Lys Leu Trp Phe Gln Asn Arg Arg Met Lys Trp Lys Lys
1               5                   10                  15

<210> SEQ ID NO 27
```

```
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Arg Glu Ile Lys Ile Trp Phe Gln Asn Arg Arg Met Lys Trp Lys Lys
1               5                   10                  15

<210> SEQ ID NO 28
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Lys Glu Thr Trp Trp Glu Thr Trp Trp Thr Glu Trp Ser Gln Pro Lys
1               5                   10                  15

Lys Arg Lys Val
            20

<210> SEQ ID NO 29
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Pro Val Ile Arg Val Trp Phe Gln Asn Lys Arg Cys Lys Asp Lys Lys
1               5                   10                  15

<210> SEQ ID NO 30
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (7)..(12)
<223> OTHER INFORMATION: This region may encompass 1-6 residues

<400> SEQUENCE: 30

Arg Arg Arg Arg Arg Arg Arg Arg Arg Arg Arg Arg
1               5                   10

<210> SEQ ID NO 31
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Leu Leu Ile Ile Leu Arg Arg Arg Ile Arg Lys Gln Ala His Ala His
1               5                   10                  15

<210> SEQ ID NO 32
<211> LENGTH: 16
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 32

Arg Arg Leu Arg Arg Leu Leu Arg Arg Leu Leu Arg Arg Leu Arg Arg
1               5                   10                  15

<210> SEQ ID NO 33
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Arg Val Gly Arg Arg Arg Arg Arg Arg Arg Arg Arg
1               5                   10

<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Arg Arg Trp Trp Arg Arg Trp Arg Arg
1               5

<210> SEQ ID NO 35
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Met Gly Leu Gly Leu His Leu Leu Val Leu Ala Ala Ala Leu Gln Gly
1               5                   10                  15

Ala Trp Ser Gln Pro Lys Lys Lys Arg Lys Val
            20                  25

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Pro Lys Lys Lys Arg Lys Val
1               5

<210> SEQ ID NO 37
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37
```

```
Arg Gly Gly Arg Leu Ser Tyr Ser Arg Arg Phe Ser Thr Ser Thr
1               5                   10                  15

Gly Arg

<210> SEQ ID NO 38
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Arg Arg Leu Ser Tyr Ser Arg Arg Phe
1               5                   10

<210> SEQ ID NO 39
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Arg Gly Gly Arg Leu Ala Tyr Leu Arg Arg Trp Ala Val Leu Gly
1               5                   10                  15

Arg

<210> SEQ ID NO 40
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Tyr Gly Arg Lys Lys Arg Arg Gln Arg Arg
1               5                   10

<210> SEQ ID NO 41
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Tyr Gly Arg Lys Lys Arg Arg Gln Arg Arg
1               5                   10

<210> SEQ ID NO 42
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gly Arg Lys Lys Arg Arg Gln Arg Arg
1               5
```

```
<210> SEQ ID NO 43
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gly Arg Lys Lys Arg Arg Gln Arg Arg Arg Pro Pro Gln
1               5                   10

<210> SEQ ID NO 44
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gly Lys Lys Lys Lys Arg Lys Arg Glu Lys Leu
1               5                   10

<210> SEQ ID NO 45
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Ser Lys Lys Lys Lys Thr Lys Val
1               5

<210> SEQ ID NO 46
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 47
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Ala Gly Tyr Leu Leu Gly Lys Ile Asn Leu Lys Ala Leu Ala Ala Leu
1               5                   10                  15

Ala Lys Lys Ile Leu
            20

<210> SEQ ID NO 48
<211> LENGTH: 12
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 48

Pro Leu Ile Tyr Leu Arg Leu Leu Arg Gly Gln Phe
1               5                   10

<210> SEQ ID NO 49
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Asp Ala Ala Thr Ala Thr Arg Gly Arg Ser Ala Ala Ser Arg Pro Thr
1               5                   10                  15

Gln Arg Pro Arg Ala Pro Ala Arg Ser Ala Ser Arg Pro Arg Arg Pro
            20                  25                  30

Val Gln

<210> SEQ ID NO 50
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(16)
<223> OTHER INFORMATION: D-amino acid

<400> SEQUENCE: 50

Lys Lys Trp Lys Met Arg Arg Asn Gln Phe Trp Ile Lys Ile Gln Arg
1               5                   10                  15

<210> SEQ ID NO 51
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(16)
<223> OTHER INFORMATION: D-amino acid

<400> SEQUENCE: 51

Lys Lys Trp Lys Met Arg Arg Asn Gln Phe Trp Leu Lys Leu Gln Arg
1               5                   10                  15

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(7)
<223> OTHER INFORMATION: Any amino acid

<400> SEQUENCE: 52
```

```
Leu Xaa Xaa Xaa Xaa Xaa Xaa
1               5

<210> SEQ ID NO 53
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Glu or any positively charged amino acid
<220> FEATURE:
<221> NAME/KEY: MOD_RES
<222> LOCATION: (5)..(5)
<223> OTHER INFORMATION: Cys or any non-polar amino acid
<220> FEATURE:
<221> NAME/KEY: MOD_RES
<222> LOCATION: (6)..(6)
<223> OTHER INFORMATION: Gln or Ala
<220> FEATURE:
<221> NAME/KEY: MOD_RES
<222> LOCATION: (9)..(9)
<223> OTHER INFORMATION: Glu or any positively charged amino acid
<220> FEATURE:
<221> NAME/KEY: MOD_RES
<222> LOCATION: (11)..(11)
<223> OTHER INFORMATION: Arg or any negatively charged amino acid
<220> FEATURE:
<221> NAME/KEY: MOD_RES
<222> LOCATION: (12)..(12)
<223> OTHER INFORMATION: Asn or any non-polar amino acid
<220> FEATURE:
<221> NAME/KEY: MOD_RES
<222> LOCATION: (16)..(16)
<223> OTHER INFORMATION: Lys or any negatively charged amino acid
<220> FEATURE:
<221> NAME/KEY: MOD_RES
<222> LOCATION: (21)..(21)
<223> OTHER INFORMATION: Ser or Ala

<400> SEQUENCE: 53

Leu Glu Gly Xaa Xaa Xaa Gly Leu Xaa Ala Xaa Xaa Arg Glu Leu Xaa
1               5                   10                  15

Glu Arg Ala Glu Xaa Val
            20

<210> SEQ ID NO 54
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Leu Glu Gly Glu Gly Gln Gly Leu Glu Ala Arg Asn Arg Glu Leu Lys
1               5                   10                  15

Glu Arg Ala Glu Ser Val
            20

<210> SEQ ID NO 55
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 55

Leu Glu Gly Glu Ala Gln Gly Leu Glu Ala Arg Asn Arg Glu Leu Lys
1               5                   10                  15

Glu Arg Ala Glu Ser Val
            20

<210> SEQ ID NO 56
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Leu Glu Gly Glu Cys Gln Gly Leu Glu Ala Arg Asn Arg Glu Leu Lys
1               5                   10                  15

Glu Arg Ala Glu Ala Val
            20

<210> SEQ ID NO 57
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Leu Glu Gly Glu Cys Gln Gly Leu Glu Ala Arg Leu Arg Glu Leu Lys
1               5                   10                  15

Glu Arg Ala Glu Ser Val
            20

<210> SEQ ID NO 58
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Leu Glu Gly Glu Cys Ala Gly Leu Glu Ala Arg Asn Arg Glu Leu Lys
1               5                   10                  15

Glu Arg Ala Glu Ser Val
            20

<210> SEQ ID NO 59
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Leu Glu Gly Arg Cys Gln Gly Leu Arg Ala Glu Asn Arg Glu Leu Glu
1               5                   10                  15

Glu Arg Ala Glu Ser Val
            20

<210> SEQ ID NO 60
<211> LENGTH: 22
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Leu Glu Gly Arg Cys Gln Gly Leu Arg Ala Glu Leu Arg Glu Leu Glu
1               5                   10                  15

Glu Arg Ala Glu Ala Val
            20

<210> SEQ ID NO 61
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Leu Glu Gly Arg Ala Gln Gly Leu Arg Ala Glu Leu Arg Glu Leu Glu
1               5                   10                  15

Glu Arg Ala Glu Ala Val
            20

<210> SEQ ID NO 62
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Leu Glu Gly Arg Leu Gln Gly Leu Arg Ala Glu Leu Arg Glu Leu Glu
1               5                   10                  15

Glu Arg Ala Glu Ala Val
            20

<210> SEQ ID NO 63
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Leu Glu Gly Arg Leu Ala Gly Leu Arg Ala Glu Leu Arg Glu Leu Glu
1               5                   10                  15

Glu Arg Ala Glu Ala Val
            20

<210> SEQ ID NO 64
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Leu Glu Gly Arg Ala Ala Gly Leu Arg Ala Glu Leu Arg Glu Leu Glu
1               5                   10                  15
```

Glu Arg Ala Glu Ala Val
            20

<210> SEQ ID NO 65
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(22)
<223> OTHER INFORMATION: D-amino acid

<400> SEQUENCE: 65

Val Ala Glu Ala Arg Glu Glu Leu Glu Arg Leu Glu Ala Arg Leu Gly
1               5                   10                  15

Gln Ala Arg Gly Glu Leu
            20

<210> SEQ ID NO 66
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Lys or Arg
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: Lys or Arg

<400> SEQUENCE: 66

Lys Xaa Xaa Xaa
1

<210> SEQ ID NO 67
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Lys or Arg
<220> FEATURE:
<221> NAME/KEY: MOD_RES
<222> LOCATION: (3)..(14)
<223> OTHER INFORMATION: Any amino acid
<220> FEATURE:
<221> NAME/KEY: MISC_FEATURE
<222> LOCATION: (3)..(14)
<223> OTHER INFORMATION: This region may encompass 10-12 residues
<220> FEATURE:
<221> NAME/KEY: MOD_RES
<222> LOCATION: (15)..(19)
<223> OTHER INFORMATION: Lys or Arg
<220> FEATURE:
<223> OTHER INFORMATION: See specification as filed for detailed
      description of substitutions and preferred embodiments

<400> SEQUENCE: 67

```
Xaa Xaa Xaa Xaa Xaa Xaa Xaa Xaa Xaa Xaa Xaa Xaa Xaa Xaa Xaa
1               5                   10                  15

Xaa Xaa Xaa

<210> SEQ ID NO 68
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Lys Arg Pro Ala Ala Thr Lys Lys Ala Gly Gln Ala Lys Lys Lys
1               5                   10                  15

<210> SEQ ID NO 69
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Val Pro Thr Leu Lys
1               5

<210> SEQ ID NO 70
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Lys Leu Pro Val Met
1               5

<210> SEQ ID NO 71
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Pro Ala Ala Lys Arg Val Lys Leu Asp
1               5

<210> SEQ ID NO 72
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Gly Arg Gly Asp Ser
1               5

<210> SEQ ID NO 73
<211> LENGTH: 6
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gly Arg Gly Asp Asn Pro
1               5

<210> SEQ ID NO 74
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
atggatgatg atatcgccgc gc                                               22

<210> SEQ ID NO 75
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
gaagcatttg cggtggacga tg                                               22

<210> SEQ ID NO 76
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
atggcgcacg ctggg                                                       15

<210> SEQ ID NO 77
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
cttgtggccc agataggcac c                                                21

<210> SEQ ID NO 78
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
gcccagactc acatcaccaa gtg                                              23

<210> SEQ ID NO 79
<211> LENGTH: 25
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
atgtttggcc tcaaaagaaa cgcgg                                              25

<210> SEQ ID NO 80
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
tcttattaga tatgccaaac cagctcctac tcc                                     33

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
atgtcactcc tggcgaccct                                                    20

<210> SEQ ID NO 82
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
gcagctacgg gtcctctgg                                                     19

<210> SEQ ID NO 83
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
atgcacctgc agcccg                                                        16

<210> SEQ ID NO 84
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
cgcgcagttg cccatgg                                                       17

<210> SEQ ID NO 85
<211> LENGTH: 18
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 85
atgggtgccc cgacgttg                                                 18

<210> SEQ ID NO 86
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
tcaatccatg gcagccagct g                                             21

<210> SEQ ID NO 87
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(12)
<223> OTHER INFORMATION: This sequence may encompass 7-12 residues

<400> SEQUENCE: 87

Arg Arg Arg Arg Arg Arg Arg Arg Arg Arg Arg Arg
1               5                   10
```

ATF5 PEPTIDE VARIANTS AND USES THEREOF

CROSS-REFERENCE TO RELATED APPLICATION

This application claims the benefit of priority of U.S. Provisional Patent Application No. 62/613,083, filed on Jan. 3, 2018.

SEQUENCE LISTING

The instant application contains a Sequence Listing which has been submitted electronically in ASCII format and is hereby incorporated by reference in its entirety. Said ASCII copy, created on Dec. 21, 2018, is named Sapience_003_US1_SL.txt and is 29,385 bytes in size.

BACKGROUND

Activating transcription factor 5 (ATF5) is a member of the ATF/CREB (cAMP response element binding protein) family of basic leucine zipper proteins. In the normal developing brain, ATF5 is highly expressed in neural progenitor/neural stem cells where it blocks cell cycle exit and promotes cell proliferation, thereby inhibiting neurogenesis and gliogenesis. ATF5 downregulation is required to permit neuroprogenitor cell cycle exit and differentiation into either neurons, astrocytes, or oligodendroglia (Greene et al. 2009; Sheng et al. 2010a; Sheng et al. 2010b; Arias et al. 2012).

In addition to its role in normal development of the nervous system, ATF5 has also emerged as an oncogenic factor that promotes survival of gliomas and other tumors. A number of studies have demonstrated that ATF5 is highly expressed in a variety of cancers, including glioblastoma, breast, pancreatic, lung, and colon cancers, and is essential for glioma cell survival (Monaco et al. 2007; Sheng et al. 2010a). In the context of gliomas, overexpression of ATF5 inversely correlates with disease prognosis and survival, i.e., glioma patients with higher ATF5 expression have significantly worse outcomes than patients with lower ATF5 expression.

In cancer cells, genes that induce apoptosis are often inactivated or down-regulated, whereas anti-apoptotic genes are frequently activated or overexpressed. Consistent with this paradigm, ATF5 upregulates transcription of anti-apoptotic proteins, including B-cell leukemia 2 (Bcl-2) and myeloid cell leukemia 1 (Mcl-1), promoting tumor cell survival (Sheng et al., 2010b; Chen et al., 2012).

SUMMARY OF THE INVENTION

Some of the main aspects of the present invention are summarized below. Additional aspects are described in the Detailed Description of the Invention, Examples, Drawings, and Claims sections of this disclosure. The description in each section of this disclosure is intended to be read in conjunction with the other sections. Furthermore, the various embodiments described in each section of this disclosure can be combined in various different ways, and all such combinations are intended to fall within the scope of the present invention.

Accordingly, the disclosure provides peptide derivatives of ATF5 comprising an ATF5 leucine zipper domain, optionally wherein an engineered enhanced leucine zipper sequence is absent, compositions and kits comprising the ATF5 peptides, and methods for inducing cytotoxicity in and/or inhibiting proliferation of a neoplastic cell using the ATF5 peptides. In particular, the disclosure provides variants of an ATF5 peptide comprising the ST-3 leucine zipper sequence (SEQ ID NO: 53), which variants can comprise non-conservative amino acid substitutions. Prior to the present invention, it could not have been predicted that such substitutions would result in molecules having similar or superior cytotoxic activity, compared with an ATF5 peptide comprising the ST-3 leucine zipper sequence (SEQ ID NO: 53). In some embodiments, the disclosure provides variants of the cell-penetrating ATF5 peptide ST-3, which variants have similar or superior cytotoxic activity, compared with ST-3.

In one aspect, the invention provides an ATF5 peptide comprising a truncated ATF5 leucine zipper region, wherein the truncated ATF5 leucine zipper region comprises a variant of the amino acid sequence LEGECQGLEARNRELKERAESV (SEQ ID NO: 53), wherein the variant is modified at one or more positions of SEQ ID NO: 53 as follows: (i) E4 is substituted with a positively charged residue; (ii) C5 is substituted with a non-polar residue; (iii) Q6 is substituted with alanine; (iv) E9 is substituted with a positively charged residue; (v) R11 is substituted with a negatively charged residue; (vi) N12 is substituted with a non-polar residue; (vii) K16 is substituted with a negatively charged residue; (viii) S21 is substituted with alanine.

In another aspect, the invention provides an ATF5 peptide comprising a truncated ATF5 leucine zipper region, wherein the truncated ATF5 leucine zipper region comprises an amino acid sequence selected from the group consisting of:

```
                                    (SEQ ID NO: 54)
LEGEGQGLEARNRELKERAESV, (SEQ ID NO: 55)
LEGEAQGLEARNRELKERAESV, (SEQ ID NO: 56)
LEGECQGLEARNRELKERAEAV (SEQ ID NO: 57)
LEGECQGLEARLRELKERAESV, (SEQ ID NO: 58)
LEGECAGLEARNRELKERAESV, (SEQ ID NO: 59)
LEGRCQGLRAENRELEERAESV, (SEQ ID NO: 60)
LEGRCQGLRAELRELEERAEAV,
and (SEQ ID NO: 61)
LEGRAQGLRAELRELEERAEAV.
```

In one embodiment, the ATF5 peptide further comprises a cell-penetrating region, such that the ATF5 peptide is a cell-penetrating peptide. In some embodiments, the cell-penetrating region has an amino acid sequence selected from the group consisting of:

```
                                    (SEQ ID NO: 25)
RQIKIWFQNRRMKWKK, (SEQ ID NO: 26)
RQLKLWFQNRRMKWKK, (SEQ ID NO: 40)
YGRKKRRQRRR,
and (SEQ ID NO: 41)
YGRKKRRQRR.
```

A further aspect of the invention provides a cell-penetrating ATF5 peptide comprising a variant of the amino acid sequence RQIKIWFQNRRMKWKKLEGECQGLEARN-RELKERAESV (SEQ ID NO: 3), wherein the variant is modified at positions of SEQ ID NO: 3 selected from the group consisting of: (i) C21G (SEQ ID NO: 4); (ii) C21A (SEQ ID NO: 5); (iii) Q22A (SEQ ID NO: 8); (iv) E20R, E25R, R27E, and K32E (SEQ ID NO: 9); (v) N28L (SEQ ID NO: 7); (vi) S37A (SEQ ID NO: 6); (vii) E20R, E25R, R27E, N28L, K32E, and S37A (SEQ ID NO: 10); and (viii) E20R, C21A, E25R, R27E, N28L, K32E, and S37A (SEQ ID NO: 11).

In certain embodiments, the ATF5 peptide comprises D-amino acids, in a reversed amino acid sequence relative to an L-amino acid sequence of an ATF5 peptide of the invention. In one embodiment, the truncated ATF5 leucine zipper region of the retro inverso peptide has a D-amino acid sequence VAEAREELERLEARLGQARGEL (SEQ ID NO: 65). In a particular embodiment, the retro inverso peptide is a cell-penetrating ATF5 peptide comprising a D-amino acid sequence (SEQ ID NO: 14)
VAEAREELERLEARLGQARGELKKWKMRRNQFWLKLQR.

In some embodiments, the ATF5 peptide of the invention does not comprise an extended leucine zipper region.

In some embodiments, the ATF5 peptide of the invention comprises an N-terminal acetyl group and/or a C-terminal amide group.

Also provided is a composition comprising an ATF5 peptide of the invention. In some embodiments, the composition is a pharmaceutical composition. Further provided is a kit comprising an ATF5 peptide of the invention, and a nucleic acid molecule encoding an ATF5 peptide of the invention.

The invention provides an ATF5 peptide of the invention for use in promoting cytotoxicity in a neoplastic cell. The invention further provides an ATF5 peptide of the invention for use in inhibiting proliferation of a neoplastic cell. The invention additionally provides a method of promoting cytotoxicity in a neoplastic cell, the method comprising contacting the neoplastic cell with an ATF5 peptide of the invention. The invention additionally provides a method of inhibiting proliferation in a neoplastic cell, the method comprising contacting the neoplastic cell with an ATF5 peptide of the invention.

BRIEF DESCRIPTION OF THE DRAWINGS

FIG. 1A-1C show amino acid sequences of the ATF-5 peptides NTAzip-ATF5 (SEQ ID NO: 1) (FIG. 1A), ST-2 (SEQ ID NO: 2) (FIG. 1B), and ST-3 (SEQ ID NO: 3) (FIG. 1C). The extended leucine zipper domain is underlined, the Penetratin cell-penetrating domain is italicized, and the ATF-5 leucine zipper domain is bolded.

DETAILED DESCRIPTION OF THE INVENTION

Figure 2:
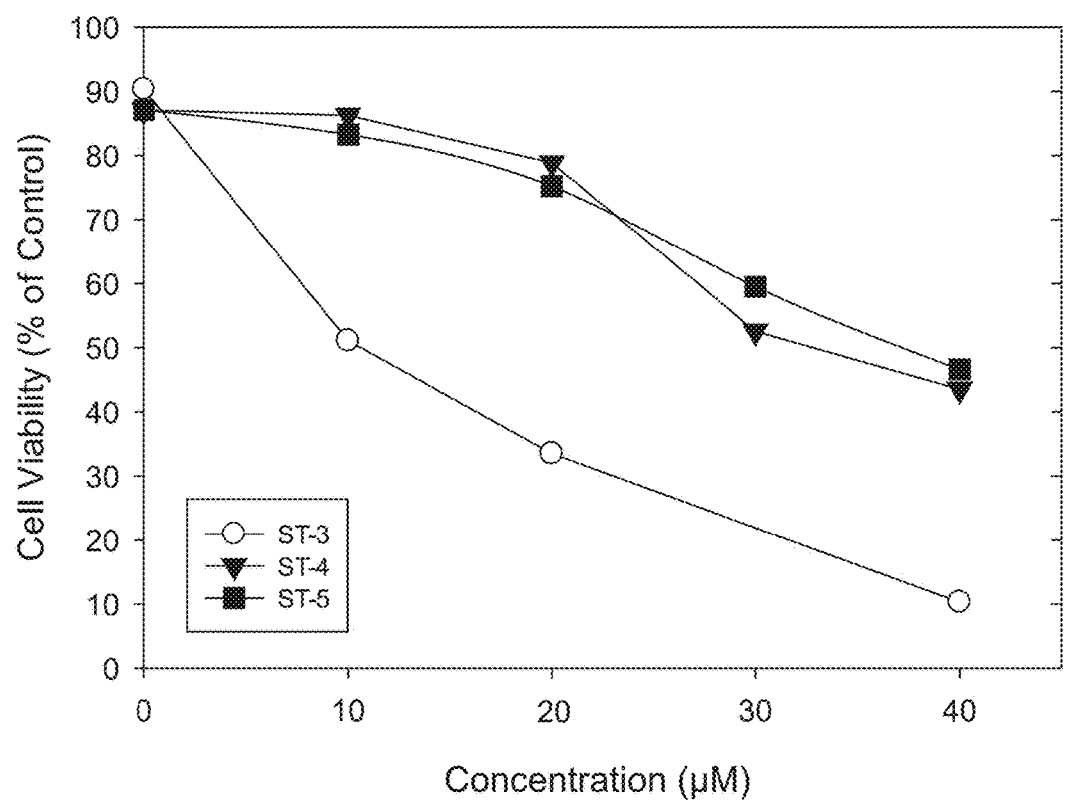
FIG. 2 shows in vitro activity of ST-3 variants in which the single cysteine is replaced.

The practice of the present invention will employ, unless otherwise indicated, conventional techniques of pharmaceutics, formulation science, protein chemistry, cell biology, cell culture, molecular biology, microbiology, recombinant DNA, and immunology, which are within the skill of the art.

In order that the present invention can be more readily understood, certain terms are first defined. Additional definitions are set forth throughout the disclosure. Unless defined otherwise, all technical and scientific terms used herein have the same meaning as commonly understood by one of ordinary skill in the art to which this invention is related.

Any headings provided herein are not limitations of the various aspects or embodiments of the invention, which can be had by reference to the specification as a whole. Accordingly, the terms defined immediately below are more fully defined by reference to the specification in its entirety.

All references cited in this disclosure are hereby incorporated by reference in their entireties. In addition, any manufacturers' instructions or catalogues for any products cited or mentioned herein are incorporated by reference. Documents incorporated by reference into this text, or any teachings therein, can be used in the practice of the present invention. Documents incorporated by reference into this text are not admitted to be prior art.

I. Definitions

The phraseology or terminology in this disclosure is for the purpose of description and not of limitation, such that the terminology or phraseology of the present specification is to be interpreted by the skilled artisan in light of the teachings and guidance.

As used in this specification and the appended claims, the singular forms "a," "an," and "the" include plural referents, unless the context clearly dictates otherwise. The terms "a" (or "an") as well as the terms "one or more" and "at least one" can be used interchangeably.

Furthermore, "and/or" is to be taken as specific disclosure of each of the two specified features or components with or without the other. Thus, the term "and/or" as used in a phrase such as "A and/or B" is intended to include A and B, A or B, A (alone), and B (alone). Likewise, the term "and/or" as used in a phrase such as "A, B, and/or C" is intended to include A, B, and C; A, B, or C; A or B; A or C; B or C; A and B; A and C; B and C; A (alone); B (alone); and C (alone).

Wherever embodiments are described with the language "comprising," otherwise analogous embodiments described in terms of "consisting of" and/or "consisting essentially of" are included.

Units, prefixes, and symbols are denoted in their Système International de Unites (SI) accepted form. Numeric ranges are inclusive of the numbers defining the range, and any individual value provided herein can serve as an endpoint for a range that includes other individual values provided herein. For example, a set of values such as 1, 2, 3, 8, 9, and 10 is also a disclosure of a range of numbers from 1-10, from 1-8, from 3-9, and so forth. Likewise, a disclosed range is a disclosure of each individual value encompassed by the range. For example, a stated range of 5-10 is also a disclosure of 5, 6, 7, 8, 9, and 10.

The terms "polypeptide," "peptide," and "protein" are used interchangeably herein to refer to polymers of amino acids of any length, and their salts. The polymer can be linear or branched, can comprise modified amino acids, and can be interrupted by non-amino acids. Except where indicated otherwise, e.g., for the abbreviations for the uncommon or unnatural amino acids set forth herein, the three-letter and one-letter abbreviations, as used in the art, are used herein to represent amino acid residues. Except when preceded with a "D" or in lower case, the amino acid is an L-amino acid. Groups or strings of amino acid abbreviations are used to represent peptides. Except where specifically indicated, peptides are indicated with the N-terminus of the left and the sequence is written from the N-terminus to the C-terminus.

The terms "polypeptide," "peptide," and "protein" also encompass an amino acid polymer that has been modified naturally or by intervention; for example, disulfide bond formation, lactam bridge formation, glycosylation, lipidation, acetylation, acylation, amidation, phosphorylation, or other manipulation or modification, such as conjugation with a labeling component or addition of a protecting group. Also included within the definition are, for example, polypeptides containing one or more analogs of an amino acid (including, for example, amino-isobutyric acid (Aib), unnatural amino acids, etc.) and polypeptides comprising or consisting of D-amino acids, as well as other modifications known in the art. In certain embodiments, the polypeptides can occur as single chains, covalent dimers, or non-covalent associated chains. Polypeptides can also be in cyclic form. Cyclic polypeptides can be prepared, for example, by bridging free amino and free carboxyl groups. Formation of the cyclic compounds can be achieved by treatment with a dehydrating agent, with suitable protection if needed. The open chain (linear form) to cyclic form reaction can involve intramolecular-cyclization. Cyclic polypeptides can also be prepared by other methods known in the art, for example, using one or more lactam bridges, hydrogen bond surrogates (Patgiri et al. 2008), hydrocarbon staples (Schafmeister et al. 2000), triazole staples (Le Chevalier Isaad et al. 2009), or disulfide bridges (Wang et al. 2006). Bridges or staples can be spaced, for example, 3, 4, 7, or 8 amino acids apart.

The term "variant" refers to a peptide having one or more amino acid substitutions, deletions, and/or insertions compared to a reference sequence. Deletions and insertions can be internal and/or at one or more termini. Substitution can include the replacement of one or more amino acids with a similar or homologous amino acid(s) or a dissimilar amino acid(s). For example, some variants include alanine substitutions at one or more amino acid positions. Other substitutions include conservative substitutions that have little or no effect on the overall net charge, polarity, or hydrophobicity of the protein. Some variants include non-conservative substitutions that change the charge or polarity of the amino acid. Substitution can be with either the L- or the D-form of an amino acid.

A "retro inverso" peptide has a reversed amino acid sequence, relative to a reference L-amino acid sequence, and is made up of D-amino acids (inverting the α-center chirality of the amino acid subunits) to help maintain side-chain topology similar to that of the original L-amino acid peptide.

The term "conservative substitution" as used herein denotes that one or more amino acids are replaced by another, biologically similar residue. Examples include substitution of amino acid residues with similar characteristics, e.g., small amino acids, acidic amino acids, polar amino acids, basic amino acids, hydrophobic amino acids, and aromatic amino acids. For further information concerning phenotypically silent substitutions in peptides and proteins, see, for example, Bowie et. al., *Science* 247:1306-1310 (1990). In the scheme below, conservative substitutions of amino acids are grouped by physicochemical properties; I: neutral and/or hydrophilic, II: acids and amides, III: basic, IV: hydrophobic, V: aromatic, bulky amino acids.

| I | II | III | IV | V |
|---|----|-----|----|----|
| A | N | H | M | F |
| S | D | R | L | Y |
| T | E | K | I | W |
| P | Q |   | V |   |
| G |   |   | C |   |

In the scheme below, conservative substitutions of amino acids are grouped by physicochemical properties; VI: neutral or hydrophobic, VII: acidic, VIII: basic, IX: polar, X: aromatic.

| VI | VII | VIII | IX | X |
|----|-----|------|----|----|
| A  | D   | H    | M  | F |
| L  | E   | R    | S  | Y |
| I  |     | K    | T  | W |
| V  |     |      | N  | H |
| P  |     |      | Q  |   |
| G  |     |      | C  |   |

Methods of identifying conservative nucleotide and amino acid substitutions which do not affect protein function are well-known in the art (see, e.g., Brummell et al., *Biochem.* 32:1180-1187 (1993); Kobayashi et al., *Protein Eng.* 12(10):879-884 (1999); and Burks et al., *Proc. Natl. Acad. Sci. U.S.A.* 94:412-417 (1997)).

The terms "identical" or percent "identity" in the context of two or more nucleic acids or peptides, refers to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms, or by visual inspection. Various algorithms and software are known in the art that can be used to obtain alignments of amino acid or nucleotide sequences.

One such non-limiting example of a sequence alignment algorithm is described in Karlin et al., *Proc. Natl. Acad. Sci.*, 87:2264-2268 (1990), as modified in Karlin et al., *Proc. Natl. Acad. Sci.*, 90:5873-5877 (1993), and incorporated into the NBLAST and XBLAST programs (Altschul et al., *Nucleic Acids Res.*, 25:3389-3402 (1991)). In certain embodiments, Gapped BLAST can be used as described in Altschul et al., *Nucleic Acids Res.* 25:3389-3402 (1997). BLAST-2, WU-BLAST-2 (Altschul et al., *Methods in Enzymology*, 266:460-480 (1996)), ALIGN, ALIGN-2 (Genentech, South San Francisco, Calif.) or Megalign (DNASTAR) are additional publicly available software programs that can be used to align sequences. In certain embodiments, the percent identity between two nucleotide sequences is determined using the GAP program in the GCG software package (e.g., using a NWSgapdna.CMP matrix and a gap weight of 40, 50, 60, 70, or 90 and a length weight of 1, 2, 3, 4, 5, or 6). In certain alternative embodiments, the GAP program in the GCG software package, which incorporates the algorithm of Needleman and Wunsch (*J. Mol. Biol.* (48):444-453 (1970)), can be used to determine the percent identity between two amino acid sequences (e.g., using either a BLOSUM 62 matrix or a PAM250 matrix, and a gap weight of 16, 14, 12, 10, 8, 6, or 4 and a length weight of 1, 2, 3, 4, 5). Alternatively, in certain embodiments, the percent identity between nucleotide or amino acid sequences is determined using the algorithm of Myers and Miller (*CABIOS* 4:11-17 (1989)). For example, the percent identity can be determined using the ALIGN program (version 2.0) and using a PAM120 with residue table, a gap length penalty of 12 and a gap penalty of 4. One skilled in the art can determine appropriate parameters for maximal alignment by particular alignment software. In certain embodiments, the default parameters of the alignment software are used. Other resources for calculating identity include methods described in *Computational Molecular Biology* (Lesk ed., 1988); *Biocomputing: Informatics and Genome Projects* (Smith ed., 1993); *Computer Analysis of Sequence Data, Part 1* (Griffin and Griffin eds., 1994); *Sequence Analysis in Molecular Biology* (G. von Heinje, 1987); *Sequence Analysis Primer* (Gribskov et al. eds., 1991); and Carillo et al., *SIAM J. Applied Math.*, 48:1073 (1988).

A "polynucleotide," as used herein can include one or more "nucleic acids," "nucleic acid molecules," or "nucleic acid sequences," and refers to a polymer of nucleotides of any length, and includes DNA and RNA. The polynucleotides can be deoxyribonucleotides, ribonucleotides, modified nucleotides or bases, and/or their analogs, or any substrate that can be incorporated into a polymer by DNA or RNA polymerase. A polynucleotide can comprise modified nucleotides, such as methylated nucleotides and their analogs. The preceding description applies to all polynucleotides referred to herein, including RNA and DNA.

An "isolated" molecule is one that is in a form not found in nature, including those which have been purified.

A "label" is a detectable compound that can be conjugated directly or indirectly to a molecule, so as to generate a "labeled" molecule. The label can be detectable on its own (e.g., radioisotope labels or fluorescent labels), or can be indirectly detected, for example, by catalyzing chemical alteration of a substrate compound or composition that is detectable (e.g., an enzymatic label) or by other means of indirect detection (e.g., biotinylation).

"Binding affinity" generally refers to the strength of the sum total of non-covalent interactions between a single binding site of a molecule and its binding partner (e.g., a receptor and its ligand, an antibody and its antigen, two monomers that form a dimer, etc.). Unless indicated otherwise, as used herein, "binding affinity" refers to intrinsic binding affinity which reflects a 1:1 interaction between members of a binding pair. The affinity of a molecule X for its partner Y can generally be represented by the dissociation constant ($K_D$). Affinity can be measured by common methods known in the art, including those described herein. Low-affinity binding partners generally bind slowly and tend to dissociate readily, whereas high-affinity binding partners generally bind faster and tend to remain bound longer.

The affinity or avidity of a molecule for its binding partner can be determined experimentally using any suitable method known in the art, e.g., flow cytometry, enzyme-linked immunosorbent assay (ELISA), or radioimmunoassay (RIA), or kinetics (e.g., KINEXA® or BIACORE™ or OCTET® analysis). Direct binding assays as well as competitive binding assay formats can be readily employed. (See, e.g., Berzofsky et al., "Antibody-Antigen Interactions," in *Fundamental Immunology*, Paul, W. E., ed., Raven Press: New York, N.Y. (1984); Kuby, *Immunology*, W.H. Freeman and Company: New York, N.Y. (1992)). The measured affinity of a particular binding pair interaction can vary if measured under different conditions (e.g., salt concentration, pH, temperature). Thus, measurements of affinity and other binding parameters (e.g., $K_D$ or Kd, $K_{on}$, $K_{off}$) are made with standardized solutions of binding partners and a standardized buffer, as known in the art.

An "active agent" is an ingredient that is intended to furnish biological activity. The active agent can be in association with one or more other ingredients. An active agent that is a peptide can also be referred to as an "active peptide."

An "effective amount" of an active agent is an amount sufficient to carry out a specifically stated purpose.

The term "pharmaceutical composition" refers to a preparation that is in such form as to permit the biological activity of the active ingredient to be effective and which contains no additional components that are unacceptably toxic to a subject to which the composition would be administered. Such composition can be sterile and can comprise a pharmaceutically acceptable carrier, such as physiological saline. Suitable pharmaceutical compositions can comprise one or more of a buffer (e.g. acetate, phosphate or citrate buffer), a surfactant (e.g. polysorbate), a stabilizing agent (e.g. polyol or amino acid), a preservative (e.g. sodium benzoate), and/or other conventional solubilizing or dispersing agents.

A "subject" or "individual" or "animal" or "patient" or "mammal," is any subject, particularly a mammalian subject, for whom diagnosis, prognosis, or therapy is desired. Mammalian subjects include humans, domestic animals, farm animals, sports animals, and laboratory animals including, e.g., humans, non-human primates, canines, felines, porcines, bovines, equines, rodents, including rats and mice, rabbits, etc.

The terms "inhibit," "block," and "suppress" are used interchangeably and refer to any statistically significant decrease in occurrence or activity, including full blocking of the occurrence or activity. For example, "inhibition" can refer to a decrease of about 10%, 20%, 30%, 40%, 50%, 60%, 70%, 80%, 90% or 100% in activity or occurrence. An "inhibitor" is a molecule, factor, or substance that produces a statistically significant decrease in the occurrence or activity of a process, pathway, or molecule.

A "neoplastic cell" or "neoplasm" typically has undergone some form of mutation/transformation, resulting in abnormal growth as compared to normal cells or tissue of the same type. Neoplasms include morphological irregularities, as well as pathologic proliferation. Neoplastic cells can be benign or malignant. Malignant neoplasms, i.e., cancers, are distinguished from benign in that they demonstrate loss of differentiation and orientation of cells, and have the properties of invasion and metastasis.

A "solid tumor" is a mass of neoplastic cells. A "liquid tumor" or a "hematological malignancy" is a blood cancer of myeloid or lymphoid lineage.

II. ATF5 Peptides and Compositions

ATF5 Peptides

ATF5 is a 282-amino acid eukaryotic transcription factor with an N-terminal acidic activation domain and a C-terminal basic leucine zipper (bZIP) domain. The bZIP domain contains a DNA-binding region and a leucine zipper region. The leucine zipper is a common structural motif, typically having a leucine at every seventh amino acid in the dimerization domain. bZIP transcription factors homo- and/or hetero-dimerize via their leucine zippers to specifically bind to DNA. Wild-type human, rat, and murine ATF5 have the amino acid sequences set forth in NCBI Accession No. NP_001180575, NP_758839, and NP_109618, respectively.

NTAzip-ATF5 (FIG. 1A) is an ATF5 peptide in which the ATF5 N-terminal activation domain is deleted and the DNA binding domain is replaced with an engineered enhanced leucine zipper, i.e., an amphipathic acidic α-helical sequence containing heptad repeats with a leucine at every seventh residue, which extends the wild-type ATF5 leucine zipper region (Angelastro et al. 2003). Cell-penetrating dominant negative ATF5 (CP-d/n-ATF5) molecules are improved versions of NTAzip-ATF5, which contain a cell-penetrating domain and a truncated ATF5 leucine zipper sequence (relative to wild-type), along with an extended leucine zipper sequence (US 2016/0046686; Karpel-Massler et al. 2016). An example of a CP-d/n ATF5 molecule is shown in FIG. 1B. As used herein, the terms "extended leucine zipper," "leucine zipper extension," and "enhanced leucine zipper" refer to a peptide having from one to four leucine heptads, i.e., Leu-$(X)_6$ (SEQ ID NO: 52), which sequence is not a wild-type ATF5 leucine zipper sequence.

ST-3 (FIG. 1C) is a variant of a CP-d/n-ATF5 molecule that lacks the leucine zipper extension, and induces cell death in neoplastic cells. Previous studies demonstrated that the enhanced leucine zipper region is required for stability and inhibitory activity of dominant-negative bZIP inhibitors (Krylov et al. 1995; Olive et al. 1997; Moll et al. 2000; Acharya et al. 2006). Therefore, the discovery that ST-3 retains its ability to specifically target and kill neoplastic cells in the absence of an extended leucine zipper region was unexpected.

The present inventors have discovered that non-conservative variants of an ATF5 peptide comprising the ST-3 leucine zipper sequence (SEQ ID NO: 53) induce cell death in neoplastic cells. The discovery that the ATF5-derived peptides of the present invention retain their ability to specifically target and kill neoplastic cells with multiple non-conservative amino acid substitutions to the ST-3 leucine zipper region could not have been predicted prior to the present invention. Retro inverso variants of ST-3 were not only active, but had increased activity relative to ST-3, which was unexpected.

The invention provides ATF5 peptides having a truncated ATF5 leucine zipper region and, optionally, a cell-penetrating region. ATF5 peptides of the invention are capable of interfering with ATF5 activity in a cell into which they are introduced. In some embodiments, the ATF5 peptide can affect pathways involved in apoptosis. ATF5 activity can be assessed by any of several assays known in the art, including the cell-kill assays described herein. ATF5 activity can also be assessed by its ability to bind to the cAMP-response element (CRE).

The "ATF5 leucine zipper region" is a truncated sequence derived from the wild-type ATF5 leucine zipper region. The term is used to refer only to sequence, and not necessarily to secondary structure. The truncated ATF5 leucine zipper region can have, for example, an amino acid sequence shown in Table 1. The ST-3 leucine zipper sequence (SEQ ID NO: 53) is shown as a point of reference. Substitutions in SEQ ID NO: 53 are shown in underlined bold type.

TABLE 1

| SEQ ID NO | 1 | 2 | 3 | 4 | 5 | 6 | 7 | 8 | 9 | 10 | 11 | 12 | 13 | 14 | 15 | 16 | 17 | 18 | 19 | 20 | 21 | 22 |
|---|---|---|---|---|---|---|---|---|---|---|---|---|---|---|---|---|---|---|---|---|---|---|
| 53 | L | E | G | E | C | Q | G | L | E | A | R | N | R | E | L | K | E | R | A | E | S | V |
| 54 | L | E | G | E | G | Q | G | L | E | A | R | N | R | E | L | K | E | R | A | E | S | V |
| 55 | L | E | G | E | A | Q | G | L | E | A | R | N | R | E | L | K | E | R | A | E | S | V |
| 56 | L | E | G | E | C | Q | G | L | E | A | R | N | R | E | L | K | E | R | A | E | A | V |
| 57 | L | E | G | E | C | Q | G | L | E | A | R | L | R | E | L | K | E | R | A | E | S | V |

TABLE 1-continued

| SEQ ID NO | 1 | 2 | 3 | 4 | 5 | 6 | 7 | 8 | 9 | 10 | 11 | 12 | 13 | 14 | 15 | 16 | 17 | 18 | 19 | 20 | 21 | 22 |
|---|---|---|---|---|---|---|---|---|---|---|---|---|---|---|---|---|---|---|---|---|---|---|
| 58 | L | E | G | E | C | A | G | L | E | A | R | N | R | E | L | K | E | R | A | E | S | V |
| 59 | L | E | G | R | C | Q | G | L | R | A | E | N | R | E | L | E | E | R | A | E | S | V |
| 60 | L | E | G | R | C | Q | G | L | R | A | E | L | R | E | L | E | E | R | A | E | A | V |
| 61 | L | E | G | R | A | Q | G | L | R | A | E | L | R | E | L | E | E | R | A | E | A | V |
| 62 | L | E | G | R | L | Q | G | L | R | A | E | L | R | E | L | E | E | R | A | E | A | V |
| 63 | L | E | G | R | L | A | G | L | R | A | E | L | R | E | L | E | E | R | A | E | A | V |
| 64 | L | E | G | R | A | A | G | L | R | A | E | L | R | E | L | E | E | R | A | E | A | V |

The leucine zipper region can be a retro inverso form. In one embodiment, the retro inverso leucine zipper region has the sequence VAEAREELERLEARLGQARGEL (SEQ ID NO: 65).

Variants of these sequences are also included in the scope of the invention. ATF5 peptides of the invention can have a leucine zipper region of at least about 60%, 61%, 62%, 63%, 64%, 65%, 66%, 67%, 68%, 69%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity to those sequences disclosed herein.

In embodiments wherein the ATF5 peptide comprises a cell-penetrating region, the cell-penetrating region is operably linked to the truncated ATF5 leucine zipper region. In some embodiments, the cell-penetrating region is covalently linked to the truncated ATF5 leucine zipper region, for example, via a peptide bond, a disulfide bond, a thioether bond, or a linker known in the art (see, e.g., Klein et al. 2014). Exemplary linkers include, but are not limited to, a substituted alkyl or a substituted cycloalkyl. Linkers can be cleavable after the peptide is delivered. A cell-penetrating region and an ATF5 leucine zipper region linked directly by an amide bond may be referred to as a "fusion." Fusions can contain an amino acid linker sequence between the cell-penetrating region and the ATF5 leucine zipper region, as discussed above with respect to active peptides. The cell-penetrating region can be linked to the N-terminus or the C-terminus of the truncated ATF5 leucine zipper region, or via a residue side chain. The cell-penetrating region and truncated ATF5 leucine zipper region can have the same or opposite chirality.

Cell-penetrating ATF5 peptides of the invention can comprise any combination of cell-penetrating and ATF5 leucine zipper domains disclosed herein. Non-limiting examples of such peptides are shown in Table 2. The cell-penetrating region is italicized. Substitutions relative to the ST-3 sequence are shown in underlined bold type.

TABLE 2

| Peptide | SEQ ID NO: | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|---|
| ST-3 | 3 | *R* | *Q* | *I* | *K* | *I* | *W* | *F* | *Q* | *N* | *R* | *R* | *M* | *K* | *W* | *K* | *K* | *L* | *E* | *G* | *E* |
| ST-4 | 4 | *R* | *Q* | *I* | *K* | *I* | *W* | *F* | *Q* | *N* | *R* | *R* | *M* | *K* | *W* | *K* | *K* | *L* | *E* | *G* | *E* |
| ST-5 | 5 | *R* | *Q* | *I* | *K* | *I* | *W* | *F* | *Q* | *N* | *R* | *R* | *M* | *K* | *W* | *K* | *K* | *L* | *E* | *G* | *E* |
| ST-6 | 6 | *R* | *Q* | *I* | *K* | *I* | *W* | *F* | *Q* | *N* | *R* | *R* | *M* | *K* | *W* | *K* | *K* | *L* | *E* | *G* | *E* |
| ST-7 | 7 | *R* | *Q* | *I* | *K* | *I* | *W* | *F* | *Q* | *N* | *R* | *R* | *M* | *K* | *W* | *K* | *K* | *L* | *E* | *G* | *E* |
| ST-8 | 8 | *R* | *Q* | *I* | *K* | *I* | *W* | *F* | *Q* | *N* | *R* | *R* | *M* | *K* | *W* | *K* | *K* | *L* | *E* | *G* | *E* |
| ST-9 | 9 | *R* | *Q* | *I* | *K* | *I* | *W* | *F* | *Q* | *N* | *R* | *R* | *M* | *K* | *W* | *K* | *K* | *L* | *E* | *G* | _R_ |
| ST-10 | 10 | *R* | *Q* | *I* | *K* | *I* | *W* | *F* | *Q* | *N* | *R* | *R* | *M* | *K* | *W* | *K* | *K* | *L* | *E* | *G* | _R_ |
| ST-11 | 11 | *R* | *Q* | *I* | *K* | *I* | *W* | *F* | *Q* | *N* | *R* | *R* | *M* | *K* | *W* | *K* | *K* | *L* | *E* | *G* | _R_ |
| ST-12 | 12 | *R* | *Q* | *I* | *K* | *I* | *W* | *F* | *Q* | *N* | *R* | *R* | *M* | *K* | *W* | *K* | *K* | *L* | *E* | *G* | _R_ |

| Peptide | SEQ ID NO: | 21 | 22 | 23 | 24 | 25 | 26 | 27 | 28 | 29 | 30 | 31 | 32 | 33 | 34 | 35 | 36 | 37 | 38 |
|---|---|---|---|---|---|---|---|---|---|---|---|---|---|---|---|---|---|---|---|
| ST-3 | 3 | C | Q | G | L | E | A | R | N | R | E | L | K | E | R | A | E | S | V |
| ST-4 | 4 | G | Q | G | L | E | A | R | N | R | E | L | K | E | R | A | E | S | V |
| ST-5 | 5 | A | Q | G | L | E | A | R | N | R | E | L | K | E | R | A | E | S | V |
| ST-6 | 6 | C | Q | G | L | E | A | R | N | R | E | L | K | E | R | A | E | A | V |
| ST-7 | 7 | C | Q | G | L | E | A | R | L | R | E | L | K | E | R | A | E | S | V |
| ST-8 | 8 | C | A | G | L | E | A | R | N | R | E | L | K | E | R | A | E | S | V |
| ST-9 | 9 | C | Q | G | L | R | A | E | N | R | E | L | E | E | R | A | E | S | V |
| ST-10 | 10 | C | Q | G | L | R | A | E | L | R | E | L | E | E | R | A | E | A | V |
| ST-11 | 11 | A | Q | G | L | R | A | E | L | R | E | L | E | E | R | A | E | A | V |
| ST-12 | 12 | A | A | G | L | R | A | E | L | R | E | L | E | E | R | A | E | A | V |

Retro inverso forms of the ATF5 peptides of the invention are also included. In one embodiment, the ATF5 peptide is ST-13, a retro inverso peptide comprising a cell-penetrating region and having the D-amino acid sequence (SEQ ID NO: 13)
VAEAREELERLEARLGQARGEL*KKWKMRRNQFWIKIQR*.

In another embodiment, the ATF5 peptide is ST-14, a retro inverso peptide comprising a cell-penetrating region and having the D-amino acid sequence (SEQ ID NO: 14)
VAEAREELERLEARLGQARGEL*KKWKMRRNQFWLKLQR*.

The cell-penetrating region is italicized. Substitutions relative to the ST-3 sequence (SEQ ID NO: 3) are shown in underlined bold type.

ATF5 peptides of the invention are preferably 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 amino acids in length, including ranges having any of those lengths as endpoints, for example, 22-38 amino acids.

ATF5 peptides of the invention include peptides having at least about 80%, 81%, 82%, 83%, 84%, 85%, 86%, 87%, 88%, 89%, 90%, 91%, 92%, 93%, 94%, 95%, 96%, 97%, 98%, or 99% identity to those sequences disclosed herein.

The ATF5 peptides can have a modified N-terminus and/or a modified C-terminus. For example, ATF5 peptides can optionally include an N-terminal acetyl group and/or a C-terminal amide group.

ATF5 peptides of the invention can optionally be cyclic. For example, ATF5 peptides can include one or more lactam bridges. A lactam bridge is preferably, but not necessarily, created between side chains spaced four amino acid residues apart (BxxxB). Lactam bridges can be formed, for example, between the side chains of Asp or Glu and Lys. Amino acid substitutions can be made at the site of the lactam bridge to facilitate the linkage.

ATF5 peptides of the invention can optionally include one or more epitope and/or affinity tags, such as for purification or detection. Non-limiting examples of such tags include FLAG, HA, His, Myc, GST, and the like. ATF5 peptides of the invention can optionally include one or more labels.

In certain aspects, the invention provides a composition, e.g., a pharmaceutical composition, comprising an ATF5 peptide of the invention, optionally further comprising one or more carriers, diluents, excipients, or other additives.

Also within the scope of the invention are kits comprising the ATF5 peptides and compositions as provided herein and, optionally, instructions for use. The kit can further contain at least one additional reagent, and/or one or more additional active agent. Kits typically include a label indicating the intended use of the contents of the kit. The term "label" includes any writing or recorded material supplied on or with the kit, or that otherwise accompanies the kit.

The ATF5 peptides of the invention promote differential gene expression of a set of genes including, but not limited to, ATF5 target genes Bcl-2, Mcl-1, and Survivin. Specifically, the ATF5 peptides knock-down expression of ATF5 target genes associated with cell survival, proliferation, and plasticity. Accordingly, the ATF5 peptides can be used to induce cell death, decrease cellular proliferation, or activate cellular differentiation. In certain embodiments, the ATF5 peptides of the invention are used to inhibit proliferation of and/or to promote cytotoxicity in a neoplastic cell. Proliferation and cytotoxicity can be measured by known assays, including the cell kill assays described herein.

Cell Targeting

ATF5 peptides of the invention can be introduced into target cells by methods known in the art. The method of introduction chosen will depend, for example, on the intended application.

In some instances, DNA or RNA encoding the ATF5 peptide can be delivered to and expressed in a target cell. Delivery can be accomplished via any suitable vector, depending on the application. Examples of vectors include plasmid, cosmid, phage, bacterial, yeast, and viral vectors prepared, for example, from retroviruses, including lentiviruses, adenoviruses, adeno-associated viruses, and envelope-pseudotyped viruses. Vectors can be introduced into cells, for example, using nanoparticles, hydrodynamic delivery, electroporation, sonoporation, calcium phosphate precipitation, or cationic polymers such as DEAE-dextran. Vectors can be complexed with lipids, such as encapsulated in liposomes, or associated with cationic condensing agents.

ATF5 peptides of the invention can be delivered to cells via mechanisms that exploit cellular receptors. Examples of such mechanisms include antibody-drug conjugates, chimeric antigen receptors, and integrin-targeting, RGD-like sequences. Examples of RGD-like sequences include GRGDS (SEQ ID NO: 72) and GRGDNP (SEQ ID NO: 73). ATF5 peptides of the invention can comprise one or more RGD-like sequences, such as two, three, four, or five RGD-like sequences, linked as described herein or by any method known in the art. The one or more RGD-like sequence(s) can be incorporated to the N-terminal or C-terminal side of the ATF5 leucine zipper region. Such RGD-like sequences can also be in retro inverso form, independently of one another and of the ATF5 leucine zipper region. Alternatively, ATF5 peptides can be encapsulated and delivered to cells in vesicles, such as exosomes or liposomes, or in micelles. Another method for introducing ATF5 peptides into cells is via cyclization, for example, using hydrocarbon staples (Bernal et al. 2007; Bird et al. 2016) or other cyclization methods known in the art.

Certain ATF5 peptides of the present invention comprise a cell-penetrating domain or cell-penetrating peptide (CPP). The terms "cell-penetrating domain," "cell-penetrating region," and "cell-penetrating peptide" are used interchangeably herein.

CPPs are short (typically about 6-40 amino acids) peptides that are able to cross cell membranes. Many CPPs are capable of crossing the blood-brain barrier (BBB). In some embodiments, the CPP is 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, or 39 amino acids in length, including ranges having any of those lengths as endpoints, for example, 10-30 amino acids. CPPs have the ability to transport covalently or non-covalently linked molecular cargo, such as polypeptides, polynucleotides, and nanoparticles, across cell membranes and the BBB. The translocation can be endocytotic or energy-independent (i.e., non-endocytotic) via translocation. Numerous CPPs are described and characterized in the literature (see, e.g., *Handbook of Cell-Penetrating Peptides* (2d ed. Ulo Langel ed., 2007); Hervé et al. 2008; Heitz et al. 2009; Munyendo et al. 2012; Zou et al. 2013; Krautwald et al. 2016). A curated database of CPPs is maintained at crdd.osdd.net/raghava/cppsite (Gautam et al. 2012).

Peptides referred to as nuclear localization sequences (NLSs) are a subset of CPPs. The classical NLS contains one (monopartite) or two (bipartite) regions of basic amino acids. Consensus sequences of classical monopartite and bipartite NLSs are, respectively, K(K/R)X(K/R) (SEQ ID NO: 66) and (K/R)(K/R)$X_{10-12}$(K/R)$_{3/5}$ (SEQ ID NO: 67), where 3/5 indicates that at least 3 of 5 consecutive amino acids are lysine or arginine (Kosugi et al. 2009). An NLS sequence from SV40 large T antigen, PKKKRKV (SEQ ID NO: 36), is an example of a classical monopartite NLS, while an NLS sequence from nucleoplasmin, KRPAATKK-AGQAKKK (SEQ ID NO: 68) is an example of a classical bipartite NLS (Lange et al. 2007; Kosugi et al. 2009). There are also numerous non-classical NLSs, such as those from ribonucleoproteins (RNPs) hnRNP A1, hnRNP K, and U snRNP (Mattaj et al. 1998).

Non-limiting examples of CPPs suitable for use in the present invention include peptides derived from proteins, such as from *Drosophila* antennapedia transcription factor (Penetratin and its derivatives RL-16 and EB1) (Derossi et al. 1998; Thorén et al. 2000; Lundberg et al. 2007; Alves et al. 2008); from HIV-1 trans-activator of transcription (Tat) (Vivès et al. 1997; Hällbrink et al. 2001); from rabies virus glycoprotein (RVG) (Kumar et al. 2007); from herpes simplex virus VP22 (Elliott et al. 1997); from antimicrobial protegrin 1 (SynB) (Rousselle et al. 2001); from rat insulin 1 gene enhancer protein (pIS1) (Kilk et al. 2001; Magzoub et al. 2001); from murine vascular endothelial cadherein (pVEC) (Elmquist et al. 2001); from human calcitonin (hCT) (Schmidt et al. 1998); and from fibroblast growth factor 4 (FGF4) (Jo et al. 2005). CPPs suitable for use in the invention also include synthetic and chimeric peptides, such as Transportan (TP) and its derivatives (Pooga et al. 1998; Soomets et al. 2000); membrane translocating sequences (MTSs) (Brodsky et al. 1998; Lindgren et al. 2000; Zhao et al. 2001), such as the MPS peptide (also known as fusion sequence-based peptide or FBP) (Chaloin et al. 1998); sequence signal-based peptide (SBP) (Chaloin et al. 1997); model amphipathic peptide (MAP) (Oehlke et al. 1998; Scheller et al. 1999; Hällbrink et al. 2001), translocating peptide 2 (TP2) (Cruz et al. 2013), MPG (Morris et al. 1997; Kwon et al. 2009), Pep-1 (Morris et al. 2001; Muñoz-Morris et al. 2007), and poly-arginine (e.g., $R_7$-$R_{12}$) (SEQ ID NO: 87) (Mitchell et al. 2000; Wender et al. 2000; Futaki et al. 2001; Suzuki et al. 2002). Representative but non-limiting sequences are shown in Table 3.

TABLE 3

| Peptide | Sequence |
| --- | --- |
| Bax-inhibiting peptide NLS1 | VPTLK (SEQ ID NO: 69) |
| Bax-inhibiting peptide NLS2 | KLPVM (SEQ ID NO: 70) |
| c-Myc NLS | PAAKRVKLD (SEQ ID NO: 71) |
| *C. elegans* SDC3 | FKKFRKF (SEQ ID NO: 15) |
| EB1 CPP | LIRLWSHLIHIWFQNRRLKWKKK (SEQ ID NO: 16) |
| FBP CPP | GALFLGWLGAAGSTMGAWSQPKKKRKV (SEQ ID NO: 17) |
| FGF4 CPP | AAVALLPAVLLALLAP (SEQ ID NO: 18) |
| HATF3 | ERKKRRRE (SEQ ID NO: 19) |
| hCT CPP | LGTYTQDFNKTFPQTAIGVGAP (SEQ ID NO: 20) |
| MAP CPP | KLALKLALKALKAALKLA (SEQ ID NO: 21) |
| MPG CPP | GLAFLGFLGAAGSTMGAWSQPKKKRKV (SEQ ID NO: 22) |
| NF-κB | VQRKRQKLMP (SEQ ID NO: 23) |
| OCT-6 | GRKKKRT (SEQ ID NO: 24) |
| Penetratin CPP | RQIKIWFQNRRMKWKK (SEQ ID NO: 25) |
| Penetratin CPP variant 1 | RQLKLWFQNRRMKWKK (SEQ ID NO: 26) |
| Penetratin CPP variant 2 | REIKIWFQNRRMKWKK (SEQ ID NO: 27) |
| Pep-1 CPP | KETWWETWWTEWSQPKKRKV (SEQ ID NO: 28) |
| pIsl CPP | PVIRVWFQNKRCKDKK (SEQ ID NO: 29) |
| Poly-Arg CPP | RRRRRR(R)$_{1-6}$ (SEQ ID NO: 30) |
| pVEC CPP | LLIILRRRIRKQAHAH (SEQ ID NO: 31) |
| RL-16 CPP | RRLRRLLRRLLRRLRR (SEQ ID NO: 32) |
| RVG CPP | RVGRRRRRRRRR (SEQ ID NO: 33) |
| $R_6W_3$ CPP | RRWWRRWRR (SEQ ID NO: 34) |
| SBP CPP | MGLGLHLLVLAAALQGAWSQPKKKRKV (SEQ ID NO: 35) |
| SV40 | PKKKRKV (SEQ ID NO: 36) |
| SynB1 CPP | RGGRLSYSRRRFSTSTGR (SEQ ID NO: 37) |
| SynB3 CPP | RRLSYSRRRF (SEQ ID NO: 38) |
| SynB5 CPP | RGGRLAYLRRRWAVLGR (SEQ ID NO: 39) |
| Tat[47-57] CPP | YGRKKRRQRRR (SEQ ID NO: 40) |

TABLE 3-continued

| Peptide | Sequence |
|---|---|
| Tat[47-56] CPP | YGRKKRRQRR (SEQ ID NO: 41) |
| Tat[48-56] CPP | GRKKRRQRR (SEQ ID NO: 42) |
| Tat[48-60] CPP | GRKKRRQRRRPPQ (SEQ ID NO: 43) |
| TCF1-α | GKKKKRKREKL (SEQ ID NO: 44) |
| TFIIE-β | SKKKKTKV (SEQ ID NO: 45) |
| TP CPP | GWTLNSAGYLLGKINLKALAALAKKIL (SEQ ID NO: 46) |
| TP10 CPP | AGYLLGKINLKALAALAKKIL (SEQ ID NO: 47) |
| TP2 CPP | PLIYLRLLRGQF (SEQ ID NO: 48) |
| VP22 CPP | DAATATRGRSAASRPTQRPRAPARSASRPRRPVQ (SEQ ID NO: 49) |

Because the function of CPPs depends on their physical characteristics rather than sequence-specific interactions, they can have the reverse sequence and/or reverse chirality as those provided in Table 3 and/or known in the art. For example, retro inverso forms of the CPPs (reverse sequence and reverse chirality) are suitable for use in the invention. One example of a retro inverso CPP has the D-amino acid sequence KKWKMRRNQFWIKIQR (SEQ ID NO: 50). Another example of a retro inverso CPP has the D-amino acid sequence KKWKMRRNQFWLKLQR (SEQ ID NO: 51). Variants of these sequences with one or more amino acid additions, deletions, and/or substitutions that retain the ability to cross cell membranes and/or the BBB are also suitable for use in the invention. The ATF5 peptides of the invention can include a cell-penetrating domain having at least about 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity to the exemplary sequences provided in Table 3. The effect of the amino acid addition(s), deletion(s), and/or substitution(s) on the ability of the CPP to mediate cell penetration can be tested using methods known in the art.

III. Methods of Preparation

ATF5 peptides of the invention can be chemically synthesized, for example, using solid-phase peptide synthesis or solution-phase peptide synthesis, or a combination of both. Synthesis may occur as fragments of the peptide which are subsequently combined either chemically or enzymatically. ATF5 polypeptides of the invention can be expressed using recombinant methods.

Accordingly, also provided are nucleic acid molecules encoding ATF5 peptides of the invention. Such nucleic acids can be constructed by chemical synthesis using an oligonucleotide synthesizer. Nucleic acid molecules of the invention can be designed based on the amino acid sequence of the desired ATF5 peptide and selection of those codons that are favored in the host cell in which the recombinant ATF5 peptide will be produced. Standard methods can be applied to synthesize a nucleic acid molecule encoding an ATF5 peptide of interest.

Once prepared, the nucleic acid encoding a particular ATF5 peptide can be inserted into an expression vector and operably linked to an expression control sequence appropriate for expression of the peptide in a desired host. In order to obtain high expression levels of the ATF5 peptide, the nucleic acid can be operably linked to or associated with transcriptional and translational expression control sequences that are functional in the chosen expression host.

A wide variety of expression host/vector combinations can be employed to anyone known in the art. Useful expression vectors for eukaryotic hosts include, for example, vectors comprising expression control sequences from SV40, bovine papilloma virus, adenovirus, and cytomegalovirus. Useful expression vectors for bacterial hosts include known bacterial plasmids, such as plasmids from *E. coli*, including pCR1, pBR322, pMB9 and their derivatives, wider host range plasmids, such as M13, and filamentous single-stranded DNA phages.

Suitable host cells include prokaryotes, yeast, insect, or higher eukaryotic cells under the control of appropriate promoters. Prokaryotes include gram negative or gram positive organisms, for example *E. coli* or bacilli. Higher eukaryotic cells can be established or cell lines of mammalian origin, examples of which include *Pichia pastoris*, 293 cells, COS-7 cells, L cells, C127 cells, 3T3 cells, Chinese hamster ovary (CHO) cells, HeLa cells, and BHK cells. Cell-free translation systems can also be employed.

EXAMPLES

Embodiments of the present disclosure can be further defined by reference to the following non-limiting examples. It will be apparent to those skilled in the art that many modifications, both to materials and methods, can be practiced without departing from the scope of the present disclosure. A number of variants to reference peptide ST-3 were made and examined, as described below.

Example 1. ST-3 Variants with Conserved Cysteine Substitution have In Vitro Activity The requirement of the single cysteine in ST-3 at amino acid position 21 for cytotoxic activity was examined using a cytotoxicity assay in HL60 cells. The cysteine residue is highly conserved within the native ATF5 domain, and is thought to be required for homodimerization of ATF5 prior to DNA binding.

HL60 PML suspension cells were set at a density of $3.5 \times 10^3$ cells/well in 150 µL of RPMI+1.5% fetal bovine serum (FBS) in a 96 well dish. ST-3, reconstituted at a concentration of 10 mg/mL in 20 mM His, pH 7.5, was added to each well at a volume of 50 μL to a final concentration range of 0-80 μM. Cells were incubated with ST-3 for 48 hours at 37° C. Cell viability was quantified by flow cytometry using an Abcam Annexin V FITC apoptosis detection kit. Briefly, cells were washed with PBS and resuspended in 1× assay buffer containing Annexin V FITC and propidium iodide (PI). Annexin V detects apoptotic cells, and PI stains dead cells. After staining, apoptotic cells show green fluorescence, dead cells show red and green fluorescence, and live cells show little or no fluorescence. Cells were selected for analysis based on forward scatter (FSC) vs. side scatter (SSC), and analyzed by BD Accuri C6 Plus flow cytometer to detect Annexin V-FITC binding (Ex=488 nm; Em=530 nm) using FITC signal detector and PI staining by the phycoerythrin emission signal detector. Percentage of Annexin $V^{low}$ and $PI^{low}$ were quantified and presented as % Viability.

Lyophilized ST-3 or ST-3 with glycine (ST-4) or alanine (ST-5) substituted for cysteine at amino acid position 21 was freshly reconstituted in histidine buffer to a stock solution of 5 mg/mL and added to cells at a final concentration range of 0-40 μM. Cells were incubated with ATF5 peptide for 48 hours prior to quantification of cell viability. Results are shown in FIG. 2.

ST-3 activity is attenuated but not ablated by substitution of cysteine at position 21 with alanine or glycine. Observed $EC_{50}$ values were approximately 16 μM, 35 μM, and 38 μM for ST-3, ST-4, and ST-5, respectively. In functional assays, $EC_{50}$ is the concentration that reduces a biological response by 50% of its maximum. In the case of ATF5 peptides, $EC_{50}$ is measured as the concentration that reduces cell viability by 50% of its maximum. $EC_{50}$ can be calculated by any number of means known in the art. Substitution of alanine for cysteine did not impact cell penetration. Penetration of the glycine-substituted variant was not tested; however, based on data for alanine substitution, cell penetration is not expected to be affected.

Example 2. ST-3 Variants with Non-Conserved Substitutions have In Vitro Activity The ST-3 variants discussed in this Example are summarized in Table 4. ST-3 has an $EC_{50}$ of about 12-20 μM.

TABLE 4

| Variant | Modification(s) | $EC_{50}$ (μM) |
| --- | --- | --- |
| ST-7 (SEQ ID NO: 7) | N28L | 3.1 |
| ST-8 (SEQ ID NO: 8) | Q22A | 5.4 |
| ST-6 (SEQ ID NO: 6) | S37A | 11.2 |
| ST-9 (SEQ ID NO: 9) | E20R, E25R, R27E, K32E | 2.0 |
| ST-10 (SEQ ID NO: 10) | E20R, E25R, R27E, N28L, K32E, S37A | 2.2 |
| ST-11 (SEQ ID NO: 11) | E20R, C21A, E25R, R27E, N28L, K32E, S37A | 4.2 |

Single Substitutions

Figure 3:
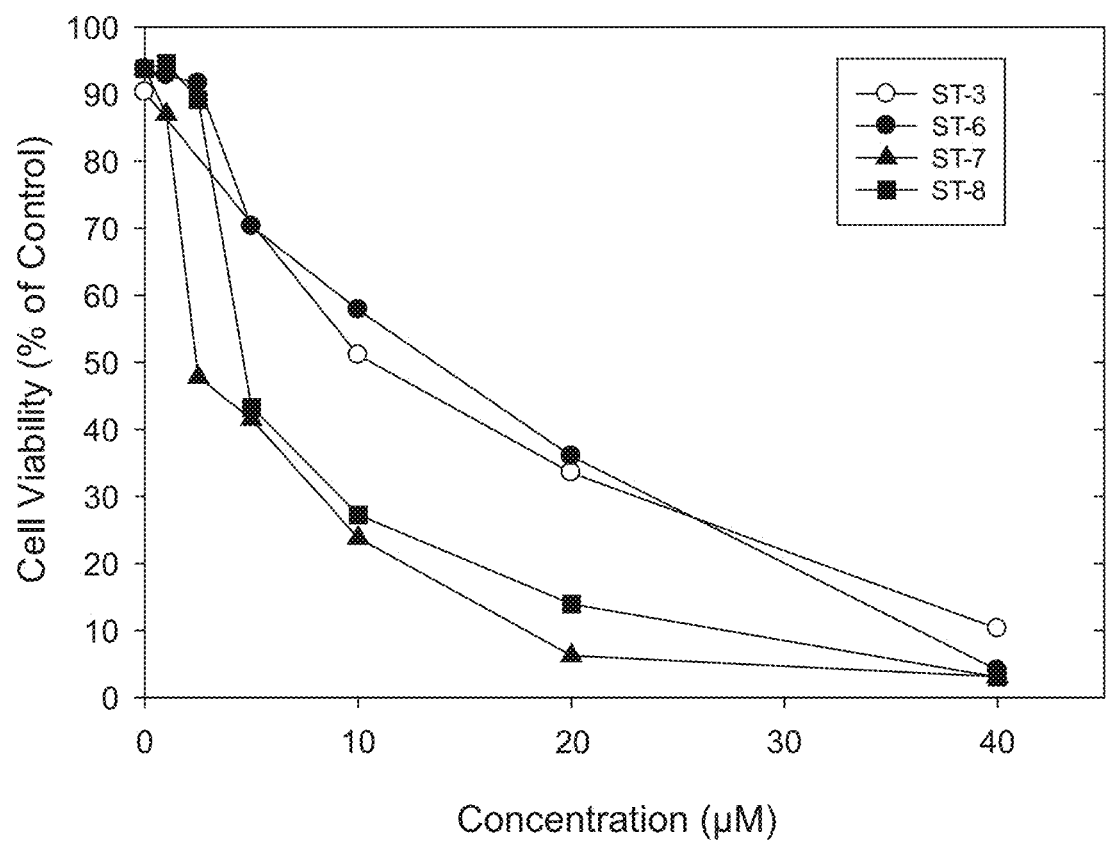
FIG. 3 shows in vitro activity of ST-3 variants in which single amino acid substitutions have been made.

Using the HL60 cell viability assay described in Example 1, we examined cytotoxic activity of ST-3 variants containing single non-conservative amino acid substitutions (FIG. 3). Variant ST-7 has a substitution of the polar asparagine with the non-polar leucine at position 28 and an $EC_{50}$ of approximately 3 μM. ST-8 has a substitution of the polar glutamine with the non-polar alanine at position 22 and an $EC_{50}$ of approximately 5 μM. This increase in activity for ST-7 and ST-8 is 3-6-fold higher than that of ST-3. ST-6 has a conservative substitution of serine with alanine at position 37 and comparable activity to ST-3.

Multiple Substitutions

Figure 4:
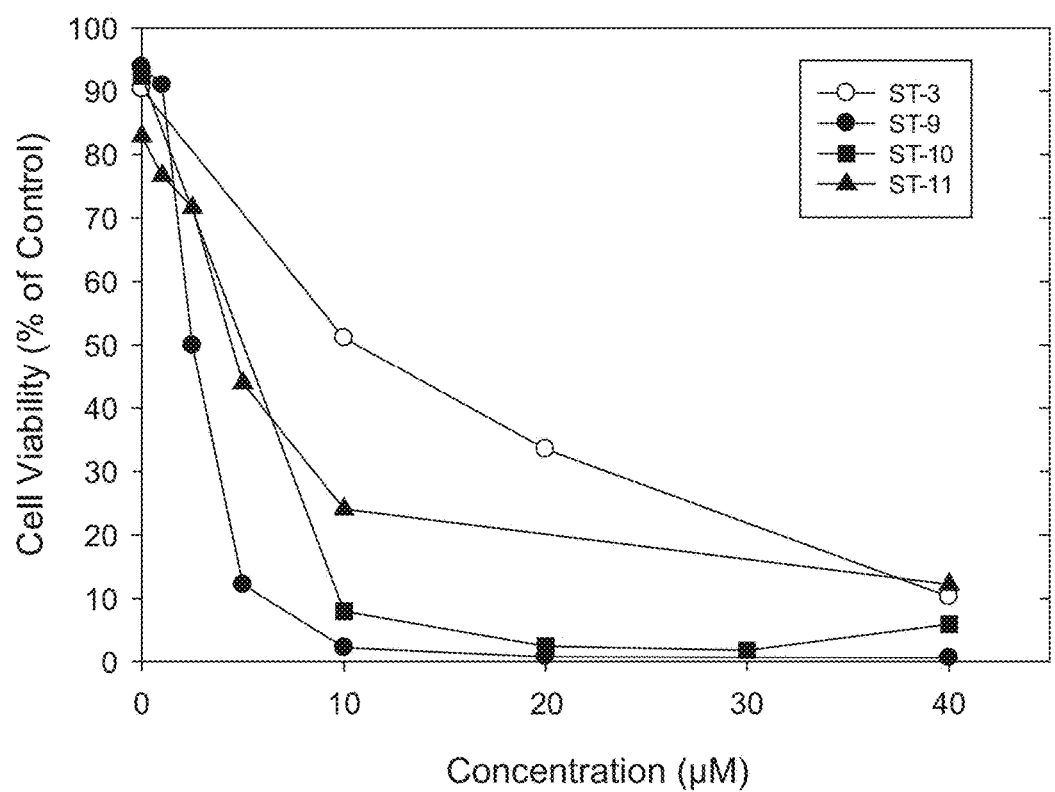
FIG. 4 shows in vitro activity of ST-3 variants in which multiple amino acid substitutions have been made.

Using the HL60 cell viability assay described in Example 1, we examined cytotoxic activity of ST-3 variants containing multiple non-conservative amino acid substitutions. Variant ST-9, has two negatively charged glutamic acid residues that were each replaced with a positively charged arginine, and a positively charged arginine and a positively charged lysine that were each replaced with a negatively charged glutamic acid. (See Table 4.) These changes involved about 18% of the ATF5 leucine zipper region of ST-3. The activity of ST-9 was significantly increased over that of ST-3 (FIG. 4). ST-9 has an $EC_{50}$ of approximately 2 compared with about 12-20 μM for ST-3.

ST-10 has the same four "charge" substitutions as ST-9, along with a non-conservative substitution of asparagine (polar) with leucine (non-polar) at position 28, as in ST-7, and a conservative substitution of serine with alanine, as in ST-6. (See Table 4.) The activity of ST-10 is comparable to that of ST-9 (FIG. 4).

ST-11 has the same substitutions as ST-10, plus a substitution of alanine for the conserved cysteine at position 21, as in ST-5. (See Table 4.) ST-11 has improved cytotoxic activity over ST-3 (FIG. 4).

Example 3. Retro Inverso ST-3 Variants have In Vitro Activity

Figure 5:
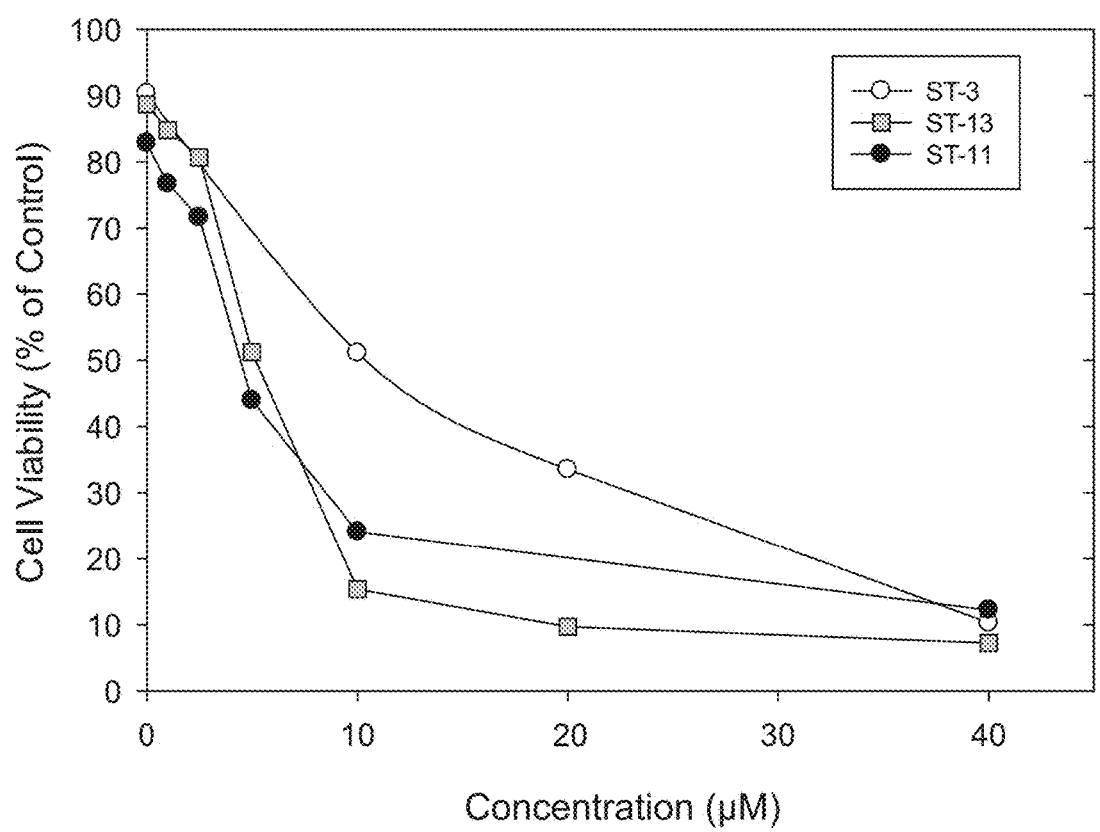
FIG. 5 shows in vitro activity of ST-13, a retro inverso version of ST-11, an ST-3 variant.
Figure 6A:
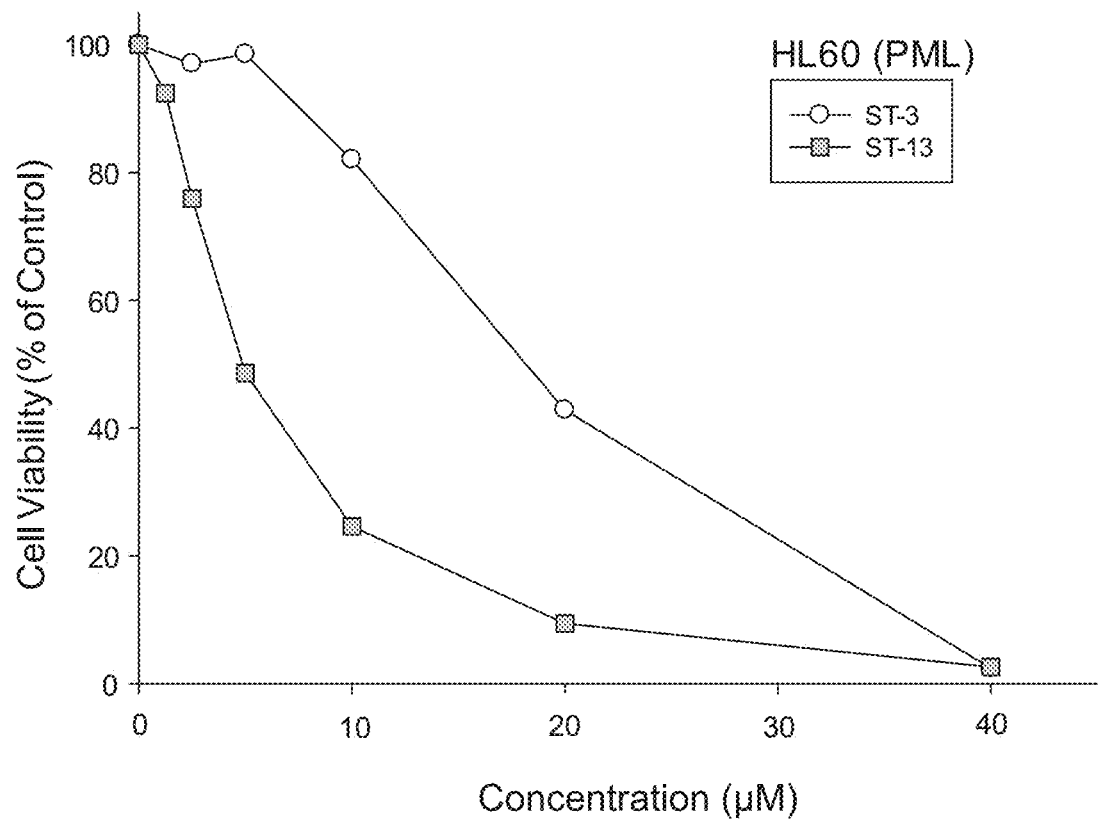
FIGS. 6A-6E show in vitro activity of ST-13 versus ST-3 in HL60 human promyelocytic leukemia cells (PML) (FIG. 6A), acute myeloid leukemia cells (AML14 and SET2) (FIGS. 6B, 6C), melanoma cells (A375) (FIG. 6D), and breast cancer cells (MCF7) (FIG. 6E). $EC_{50}$ values in each cell type for ST-3 and ST-13, respectively, were 19.0 μM and 4.8 μM (FIG. 6A); 29.6 μM and <1 (FIG. 6B); 98.2 μM and 17.7 (FIG. 6C); 21.8 μM and 1.4 μM (FIG. 6D); and 52.9 μM and <1 (FIG. 6E).
Figure 6B:
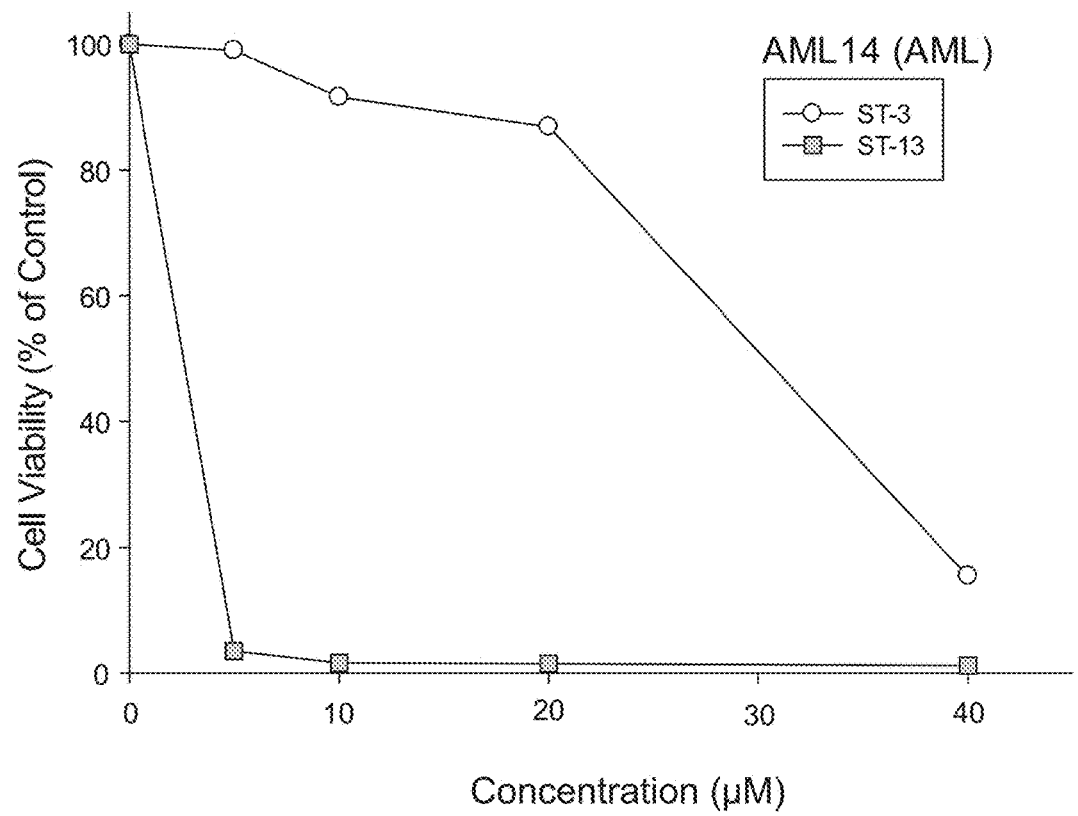
Figure 6C:
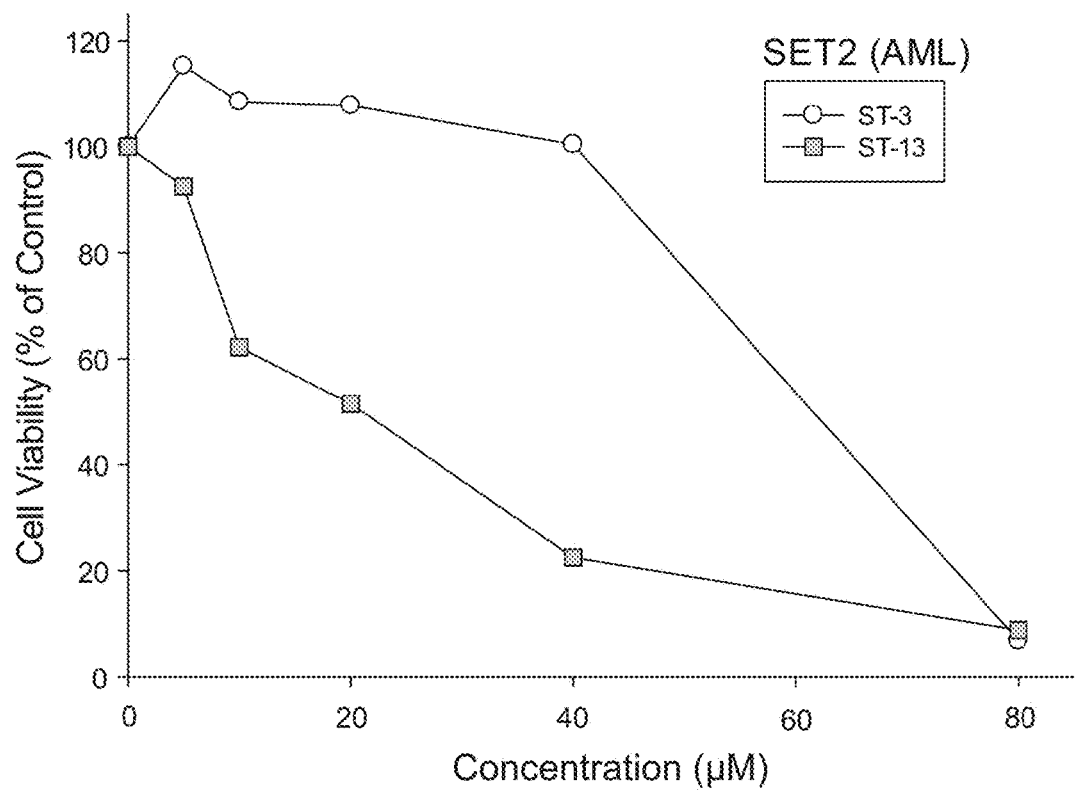
Figure 6D:
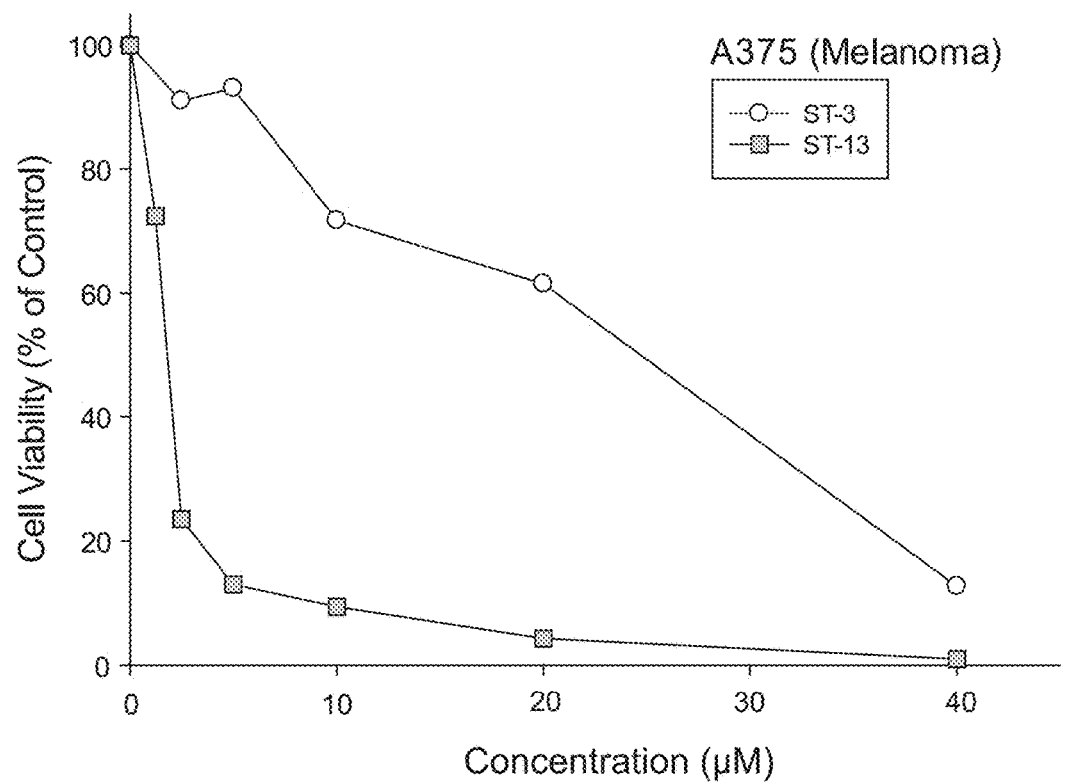
Figure 6E:
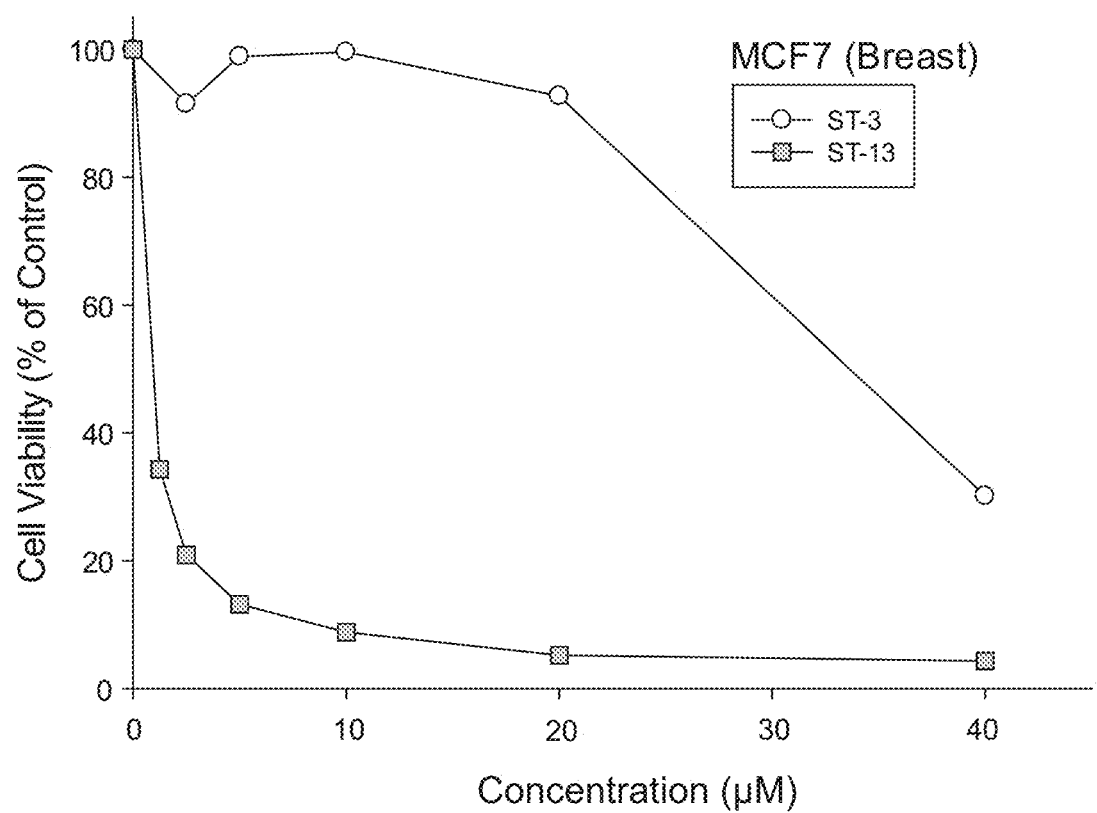
Figure 7A:
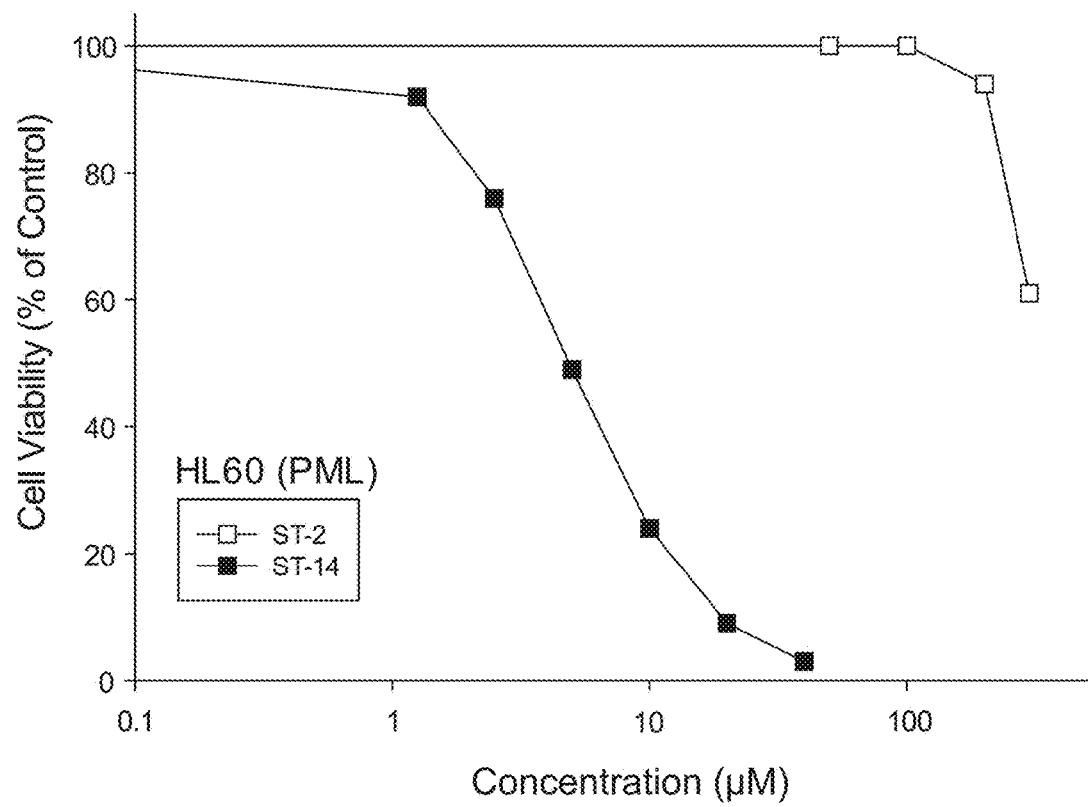
FIGS. 7A-7E show in vitro activity of ST-14 in HL60 human promyelocytic leukemia cells (PML) (FIG. 7A), acute myeloid leukemia cells (AML14) (FIG. 7B), glioblastoma cells (U251) (FIG. 7C), melanoma cells (A375) (FIG. 7D), and breast cancer cells (MCF7) (FIG. 7E). $EC_{50}$ value for ST-2 and ST-14, respectively, were >300 and <5 μM (FIG. 7A).
Figure 7B:
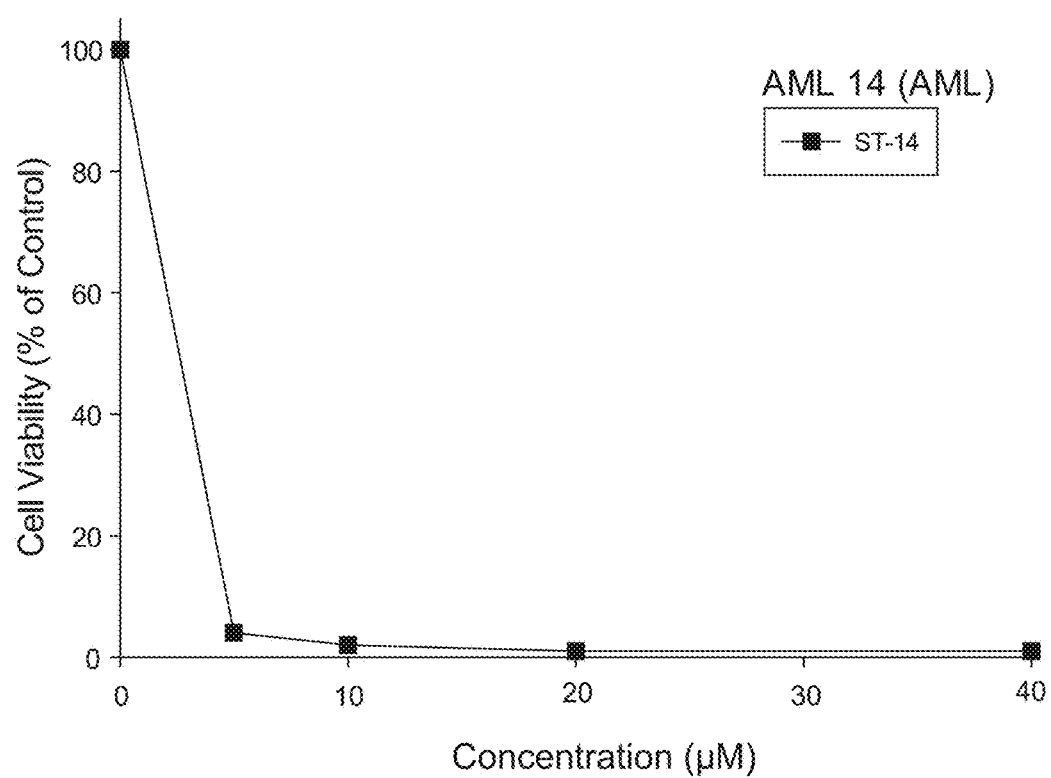
Figure 7C:
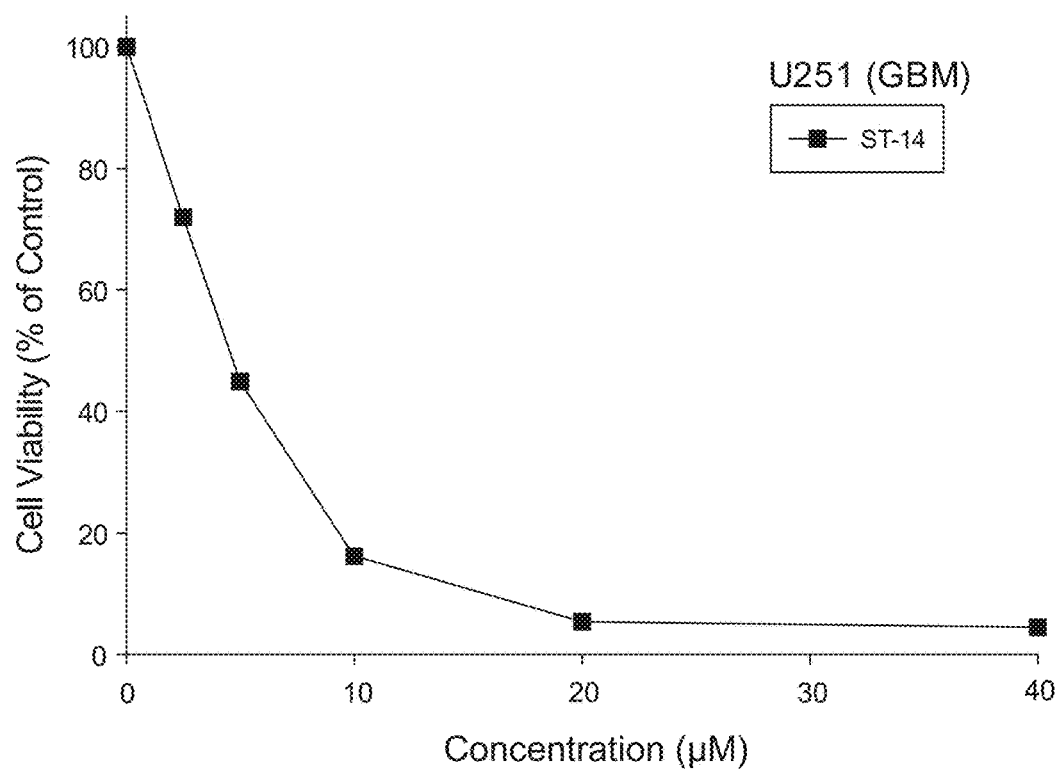
Figure 7D:
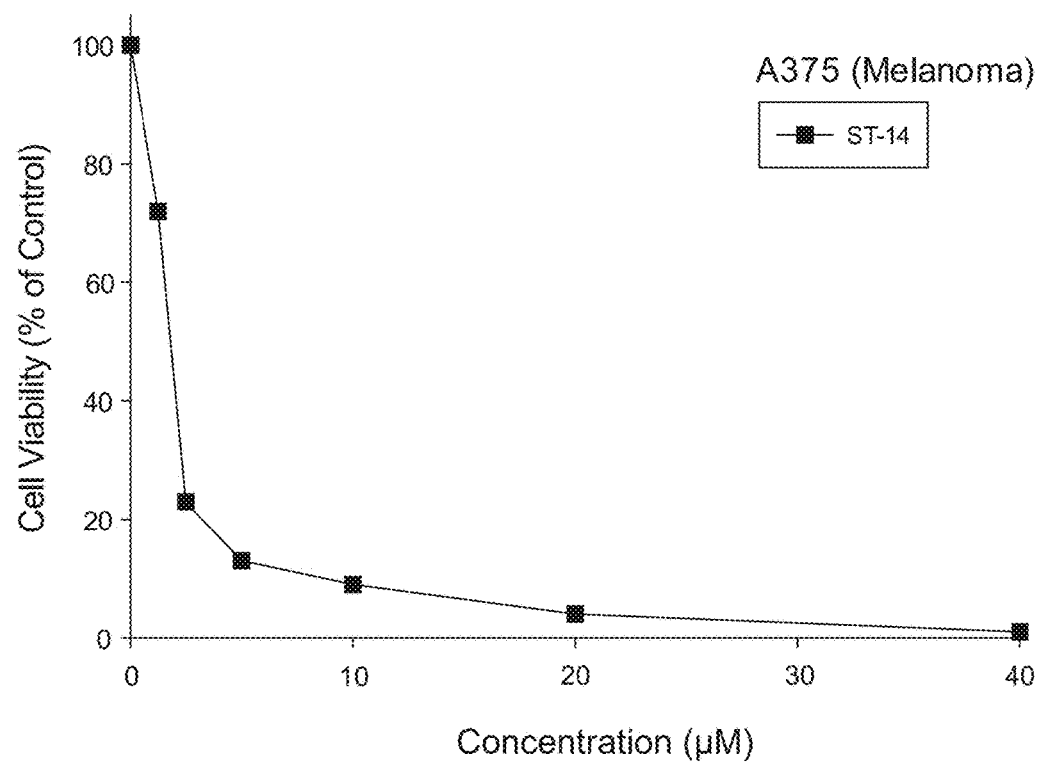
Figure 7E:
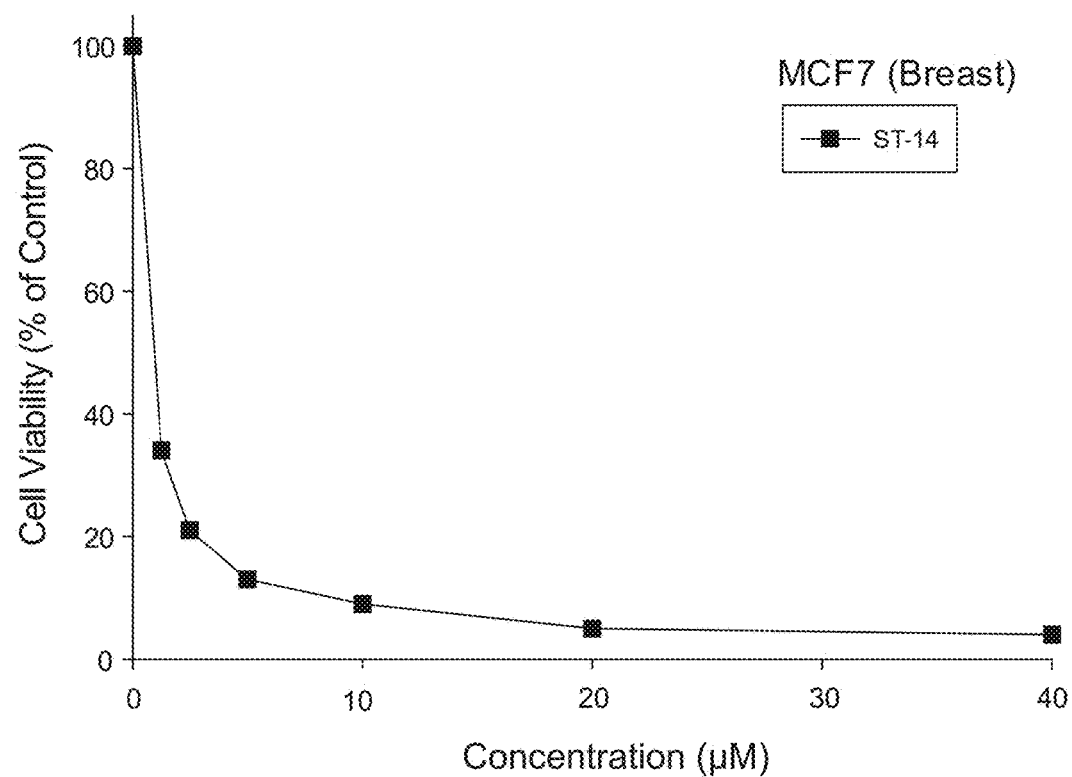
Figure 8A:
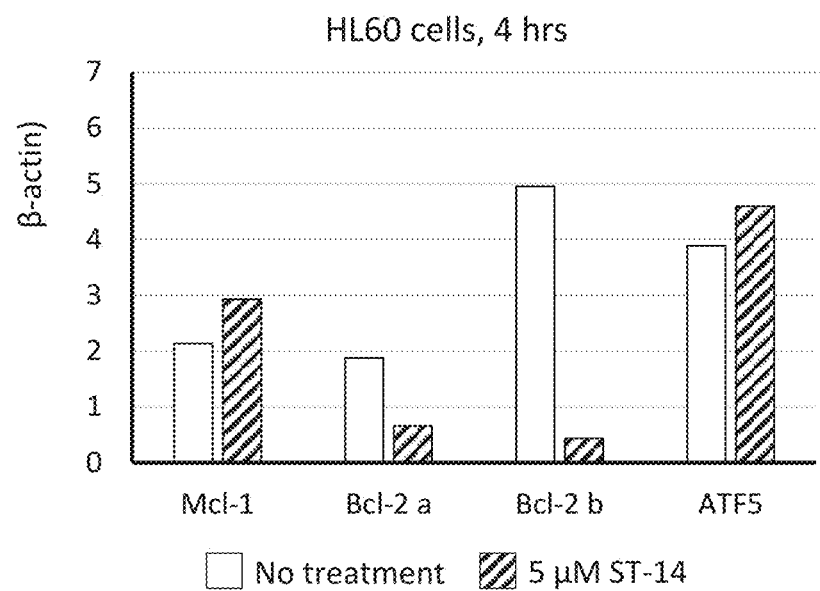
FIGS. 8A-8D show that treatment with ST-14 downregulates expression of Mcl-1, Bcl-2, BIRC5 (Survivin), and ATF5. RNA expression was measured by reverse transcription polymerase chain reaction (RT-PCR). Expression levels in HL60 cells treated with 5 μM ST-14 are shown relative to β-actin expression at 4 hours (FIG. 8A) and 24 hours (FIG. 8B) post-treatment. Expression levels in U251 cells (FIG. 8C) and HL60 cells (FIG. 8D) treated with 0, 20, or 40 μM ST-14 are shown relative to β-actin expression after 4 hours (FIG. 8C) or 24 hours (FIG. 8D) of treatment.
Figure 8B:
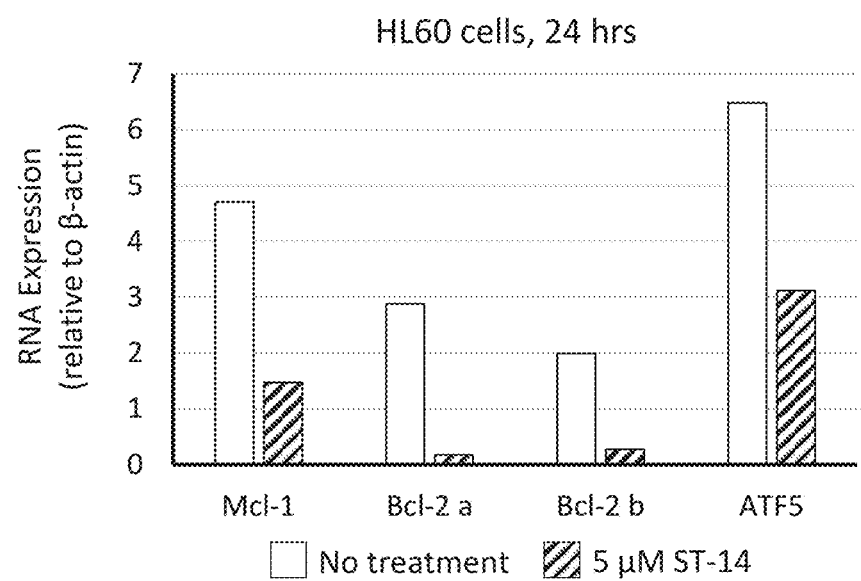
Figure 8C:
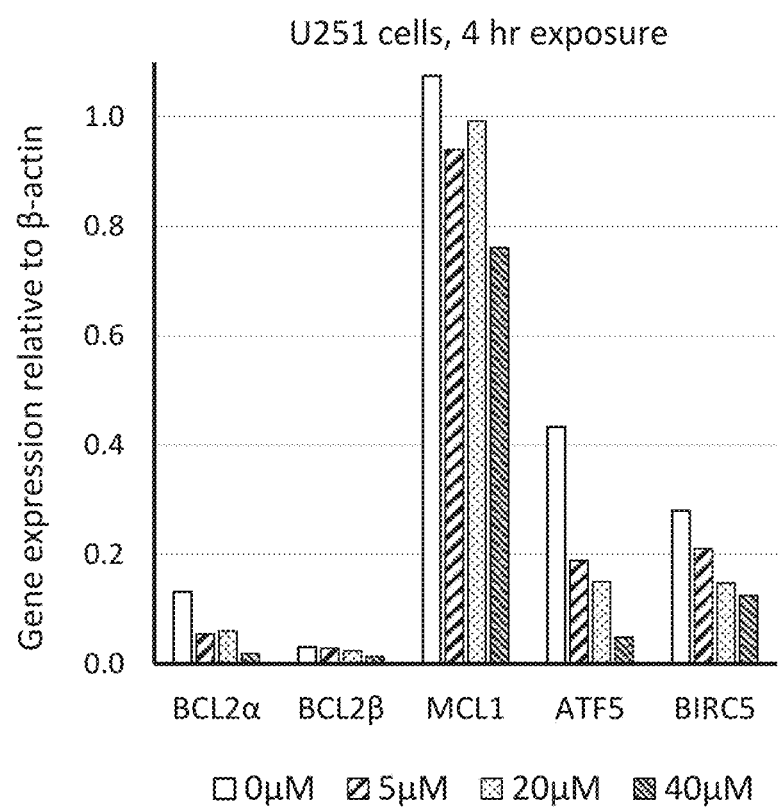
Figure 8D:
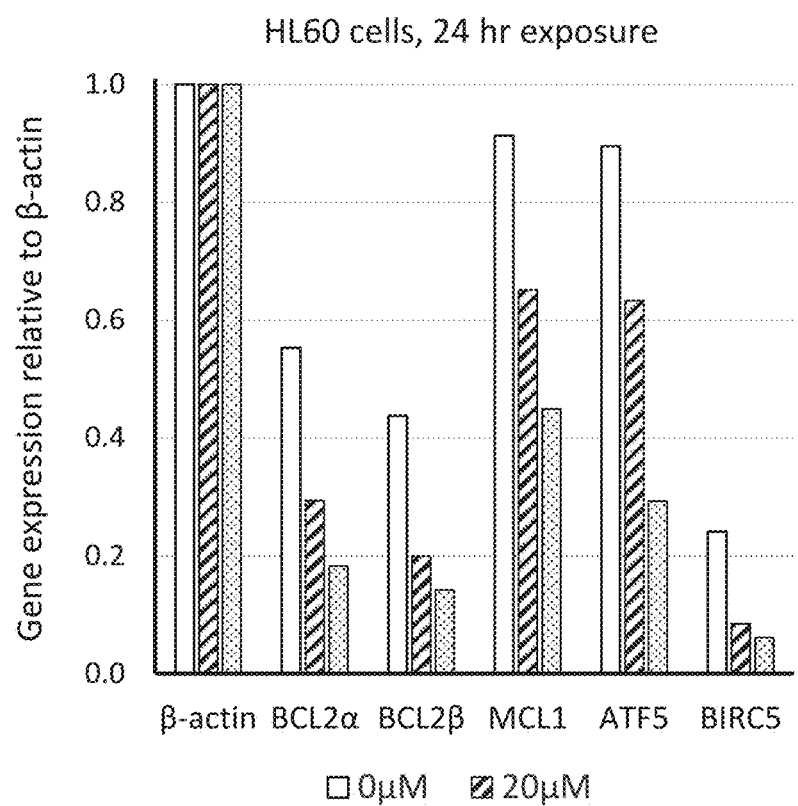

We examined the cytotoxicity of a retro inverso form of ST-11 in the HL60 cell viability assay described in Example 1. The retro inverso variant, ST-13, had comparable activity to ST-11, and superior activity to ST-3 (FIG. 5).

ST-13 was further examined in various human cancer cell lines, as was a second retro-inverso variant, ST-14. Suspension cells (HL60, AML14, or SET2) were set at a density of $3.5 \times 10^3$ cells/well in 150 μL of RPMI+1.5% fetal bovine serum (FBS) in a tissue culture-treated 96 well dish. ATF5 peptide, reconstituted at a concentration of 10 mg/mL in 20 mM His, pH 7.5, was added to each well at a volume of 50 μL to a final concentration range of 0-80 μM. Cells were incubated with peptide for 48 hours at 37° C. Cell viability was quantified by flow cytometry using an Abcam Annexin V FITC apoptosis detection kit. Briefly, cells were washed with PBS and resuspended in 1× assay buffer containing Annexin V FITC and propidium iodide (PI). Cells were analyzed by BD Accuri C6 Plus flow cytometer to detect Annexin V-FITC binding (Ex=488 nm; Em=530 nm) using FITC signal detector, and to detect PI staining using the phycoerythrin emission signal detector. Percentage of Annexin $V^{low}$ and $PI^{low}$ were quantified and presented as % Viability. $EC_{50}$ values were calculated using GraphPad Prism v.7 XML.

Additionally, adherent A375, MCF7, U251, DU145, U87, and A549 cells were set at a density of $3.5 \times 10^3$ cells/well in 200 μL of media on day −1. On day 0, media was removed and replenished with 150 μL of fresh media, and cells were treated with ATF5 peptide as described. Following a 48-hour incubation at 37° C., floating cells were collected, adherent cells were washed with Dulbecco's Phosphate Buffered Saline (DPBS), dissociated from the dish with 50 μL 2.5% trypsin at RT, and combined with floating cells. Cell viability was determined as described above for suspension cells or by MTT assay (MCF7 cells). Alternatively, cells were gently removed from the cell culture plate following trypsinization with 2.5% trypsin, and cell viability was quantified by flow cytometry using an Abcam Annexin V FITC apoptosis detection kit, as described above.

PBMC and BMMC were cultured under the conditions described above for suspension cells.

Both ST-13 (FIGS. 6A-6E) and ST-14 (FIGS. 7A-7E; Table 5) showed significant cytotoxic activity in a wide range of tumor cell types; ST-14 was also cytotoxic in peripheral blood mononuclear cells (PBMC) and bone marrow mononuclear cells (BMMC) (Table 5).

TABLE 5

| Cell Line | ST-14 Calculated EC$_{50}$ (μM) |
| --- | --- |
| HL60 | 9.2 |
| AML14 | 4.8 |
| A375 | 0.7 |
| MCF7 | 2.1 |

TABLE 5-continued

| Cell Line | ST-14 Calculated EC$_{50}$ (μM) |
| --- | --- |
| U251 | 2.2 |
| U87 | 3.6 |
| DU145 | 4.0 |
| A549 | 1.2 |
| SET2 | 22.1 |
| PBMC | >80 |
| BMMC | >80 |

We measured RNA expression of ATF5 and apoptosis regulatory proteins, Mcl-1, Bcl-2, and Survivin, relative to β-actin expression in HL60 cells following treatment with ST-14. Briefly, 8×10$^5$ HL60 suspension cells were plated in a 6-well plate and treated with 0 μM, 5 μM, 20 μM, or 40 μM ST101 for 4 or 24 hours. Cells were centrifuged at 1,200 rpm for 7.5 minutes, and pellets were washed with 750 μM DNAse-RNAse-free H$_2$O to remove residual media. RNA was extracted using Quick-RNA™ MiniPrep Plus kit (Zymo Research Cat. #R1054) according to the manufacturer's instructions and eluted with 55 μM H$_2$O. RNA (200 ng) was run on Invitrogen pre-cast 2% SYBR™ Gold E-Gel (Thermo Fisher Scientific Cat. #G401002) to assess RNA quality. cDNA was synthesized using Invitrogen SuperScript™ IV VILO Master Mix with ezDNAse™ Enzyme (Thermo Fisher Scientific Cat. #11766050) according to manufacturer's protocol with the following modification: the cDNA was extended at 56° C. instead of 50° C. Minus RT controls were set up to rule out gDNA contamination. cDNA was amplified using gene-specific primers (Table 6) and KOD Xtreme™ Hot Start DNA Polymerase (Millipore Sigma Cat. #71975-3). An equal amount of RNA was added to each reaction. All PCR products were run on Invitrogen pre-cast 2% ethidium bromide E-Gel (Thermo Fisher Scientific). Gene expression was compared to β-actin using BioRad ImageLab software.

TABLE 6

| Gene | Primer | Sequence | SEQ ID NO |
| --- | --- | --- | --- |
| β-Actin | hsACTB_F | ATG GAT GAT GAT ATC GCC GCG C | 74 |
| β-Actin | hsACTB_R | GAA GCA TTT GCG GTG GAC GAT G | 75 |
| Bcl2α, β | hsBcl2 alpha beta_F | ATG GCG CAC GCT GGG | 76 |
| Bcl2α | hsBcl2 alpha_R | CTT GTG GCC CAG ATA GGC ACC | 77 |
| Bcl2β | hsBcl2 beta_R | GCC CAG ACT CAC ATC ACC AAG TG | 78 |
| Mcl1 | hsMcl1_F | ATG TTT GGC CTC AAA AGA AAC GCG G | 79 |
| Mcl1 | hsMcl1_R | TCT TAT TAG ATA TGC CAA ACC AGC TCC TAC TCC | 80 |
| ATF5 | hsATF5_F | ATG TCA CTC CTG GCG ACC CT | 81 |
| ATF5 | hsATF5_R | GCA GCT ACG GGT CCT CTG G | 82 |
| CEP13β | hsCEBP beta_F | ATG CAC CTG CAG CCC G | 83 |
| CEP13β | hsCEBP beta_R | CGC GCA GTT GCC CAT GG | 84 |
| Birc5 | hsBIRC5_F | ATG GGT GCC CCG ACG TTG | 85 |
| Birc5 | hsBIRC5_R | TCA ATC CAT GGC AGC CAG CTG | 86 |

ST-14 exposure resulted in reduced expression of Mcl-1, Bcl2, and BIRC5 (Survivin), relative to β-actin expression (FIGS. 8A-8D).

Example 4. ST-3 Variants have In Vivo Activity

Figure 9:
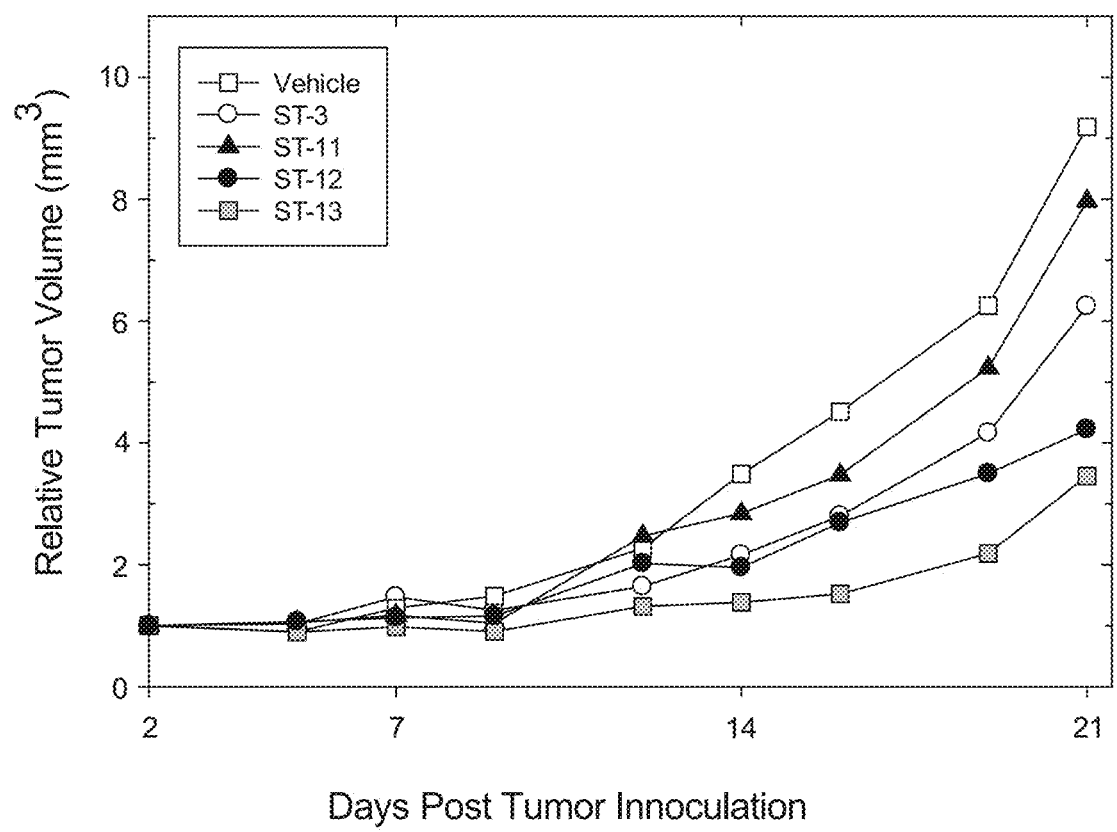
FIG. 9 shows the anti-tumor activity of ST-3 variants in an HL60 subcutaneous tumor model. Nu/J mice were treated with 25 mg/kg BID-IP (n=6-7 per group).

We examined the effect of ST-3 and three variants on tumor volume in a HL60 subcutaneous tumor model. Briefly, 5×10$^6$ HL60 cells, suspended 1:1 in Matrigel, were implanted via subcutaneous injection into the axilla of NU/J mice. Dosing was initiated on day 2 post tumor inoculation, with average tumor volume ranging from 144-176 mm$^3$. ATF5 peptides were administered at a dose of 25 mg/kg via intraperitoneal (IP) injection twice a day. All of the tested variants reduced tumor volume relative to vehicle, with the retro inverso variant, ST-13, showing the greatest anti-tumor activity (FIG. 9).

We examined the effect of ST-14 on tumor volume in tumor models using U251 glioblastoma cells, MCF7 breast cancer cells, HL60 promyelocytic leukemia cells, and A375 melanoma cells. Briefly, 5×10$^6$ cells, suspended 1:1 in Matrigel, were implanted via subcutaneous injection into the axilla of NU/J mice (for MCF7 and HL60 cells) or NOD/SCID mice (for U251 and A375 cells).

Figure 10A:
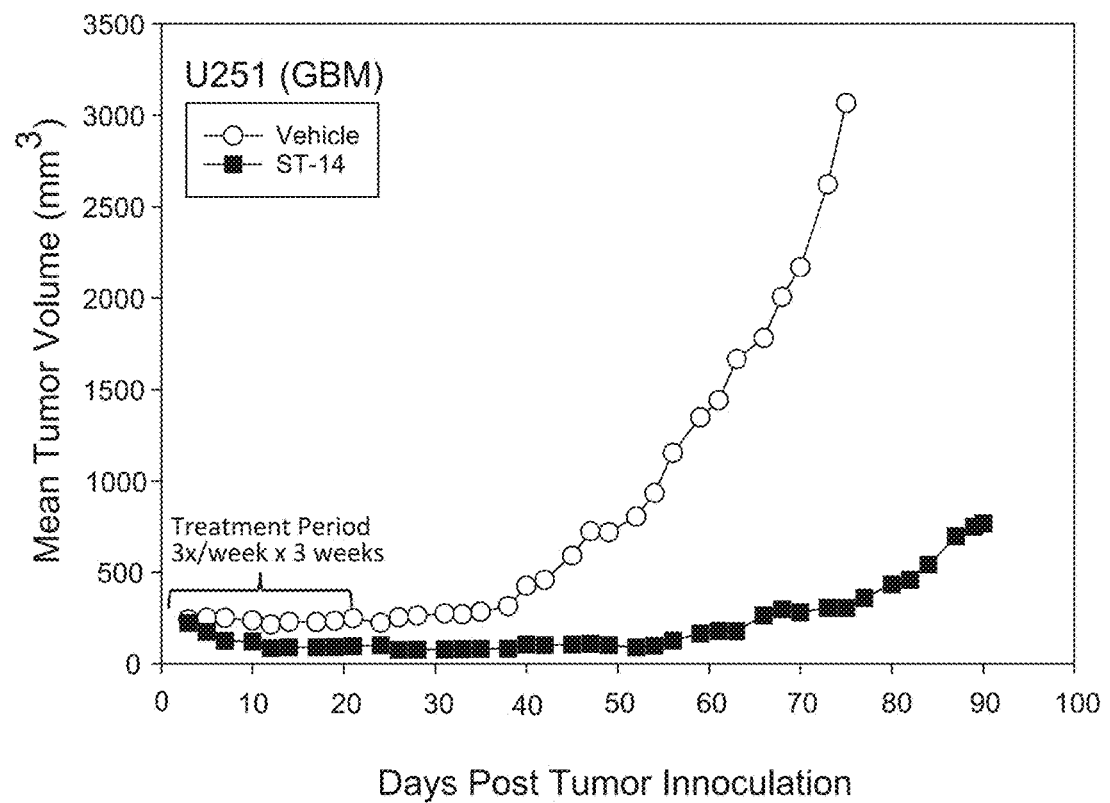
FIGS. 10A-10C show anti-tumor activity of ST-14 in a U251 subcutaneous tumor model. NOD/SCID mice were treated with 50 mg/kg SC three times per week for three weeks. Average starting tumor volume was about 240 mm³. Mean tumor volume (FIG. 10A), percent survival (FIG. 10B), and individual tumor volumes (FIG. 10C) are shown. Data points represent mean±SEM; p<0.0001; n=number of live animals per group at each timepoint.
Figure 10B:
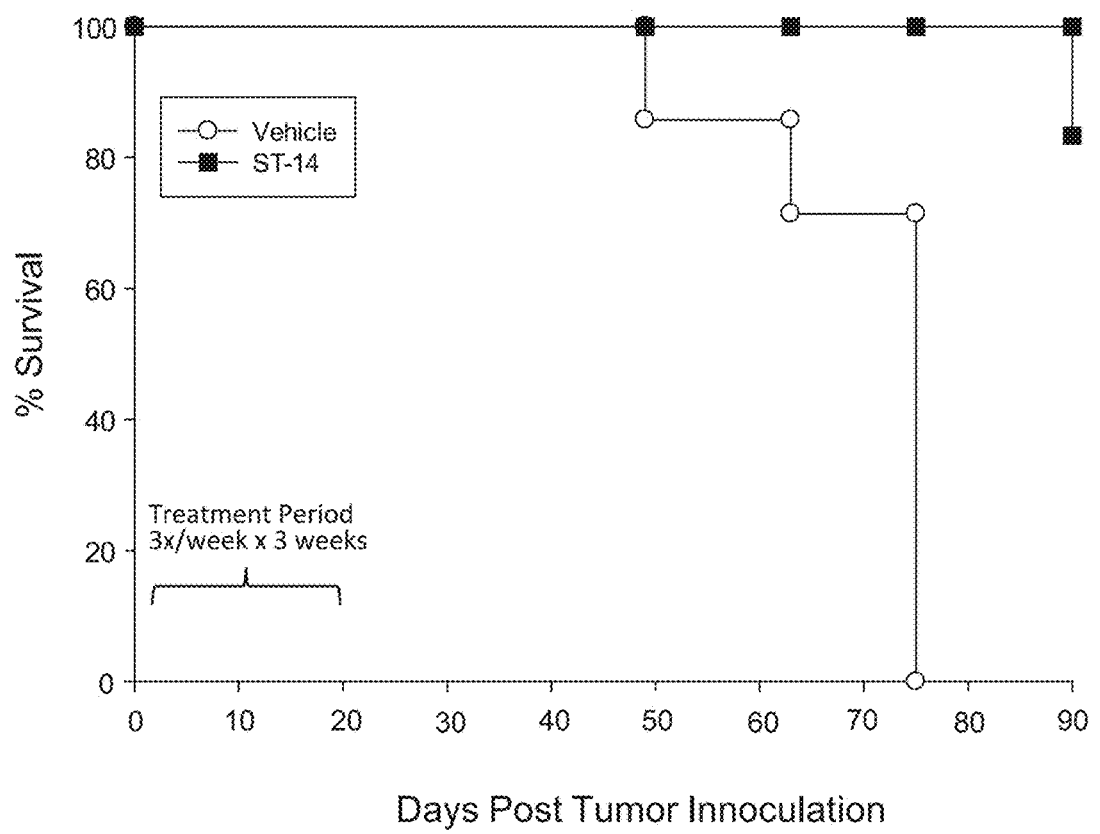
Figure 10C:
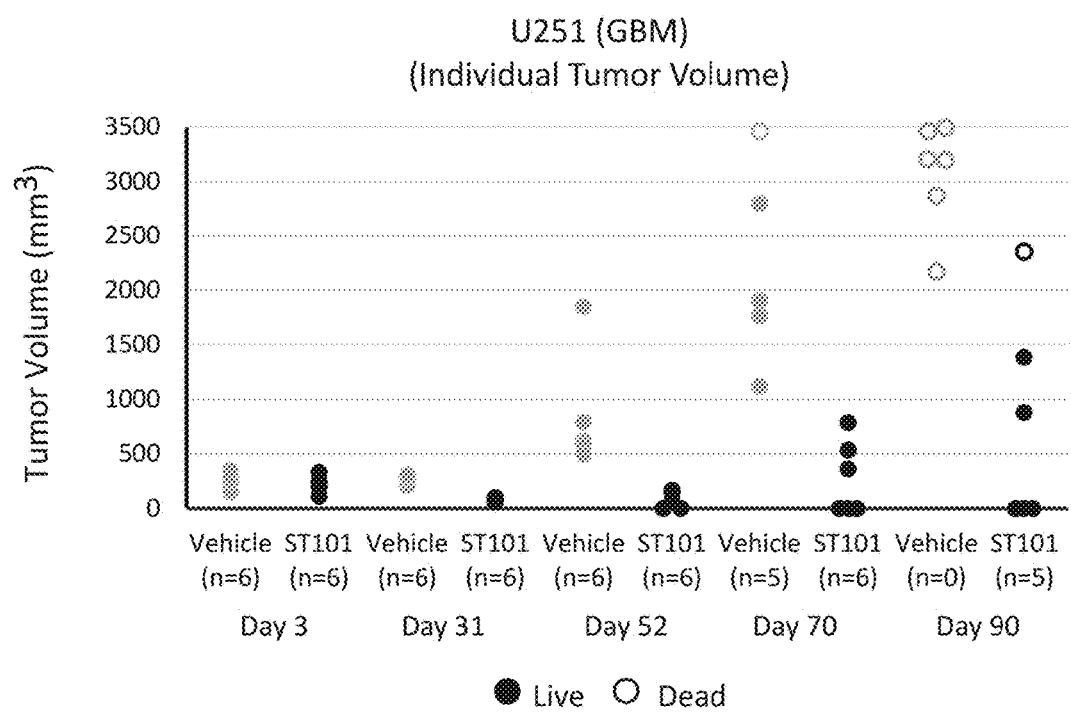

For U251 cell tumors, dosing was initiated on day 2 post tumor inoculation, with average tumor volume of about 240 mm$^3$. ST-14 was administered at a dose of 50 mg/kg via subcutaneous (SC) injection three times per week for three weeks. ST-14 significantly reduced tumor volume (FIGS. 10A, 10C) and increased survival (FIGS. 10B-10C) relative to vehicle. Similar results were achieved with a dose of 25 mg/kg ST-14.

Figure 11A:
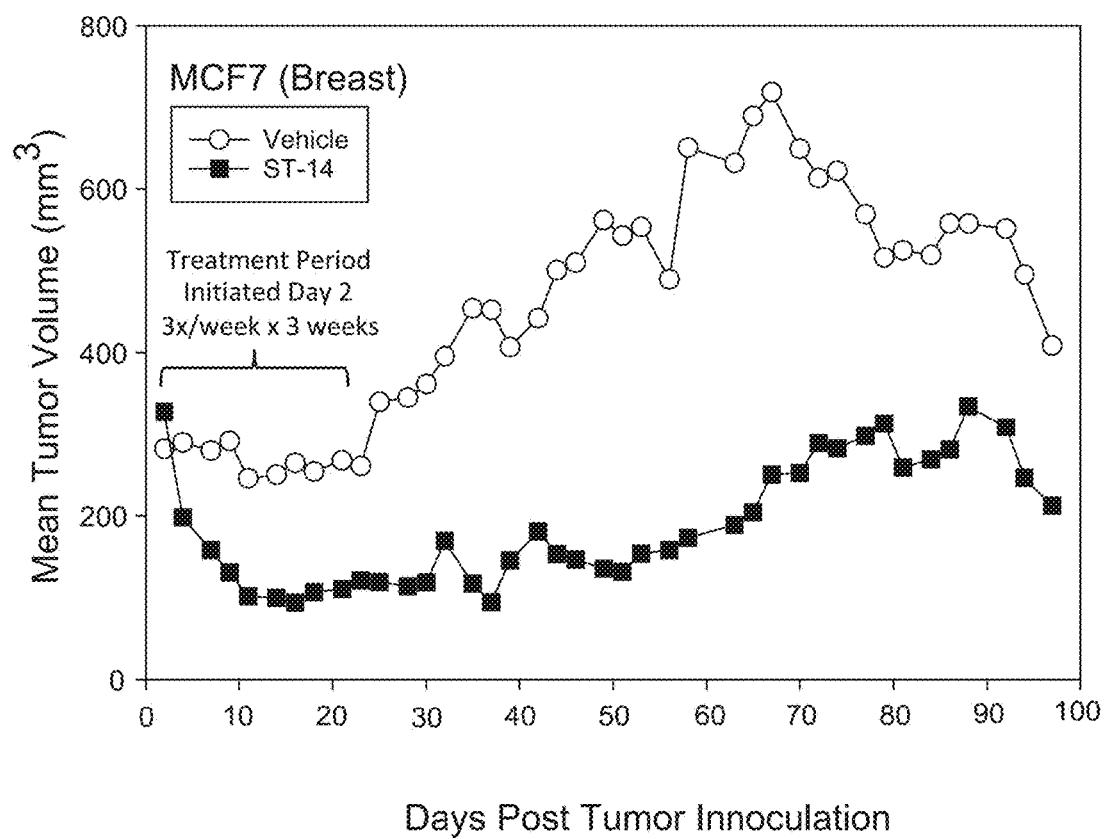
FIGS. 11A-11B show that early or delayed ST-14 administration has significant anti-tumor activity in MCF7 breast cancer cells. Nu/J mice were treated with 25 mg/kg SC three times per week for three weeks beginning 2 days (FIG. 11A) or 59 days (FIG. 11B) post tumor inoculation. Average starting tumor volume was about 280-330 mm³. Inoculation: 2×10⁶ cells in Vehicle groups (FIGS. 11A, 11B); 2×10⁶ cells in ST-14 group (FIG. 11A); 5×10⁶ cells in ST-14 group (FIG. 11B). Data points represent mean±SEM; p<0.0001.
Figure 11B:
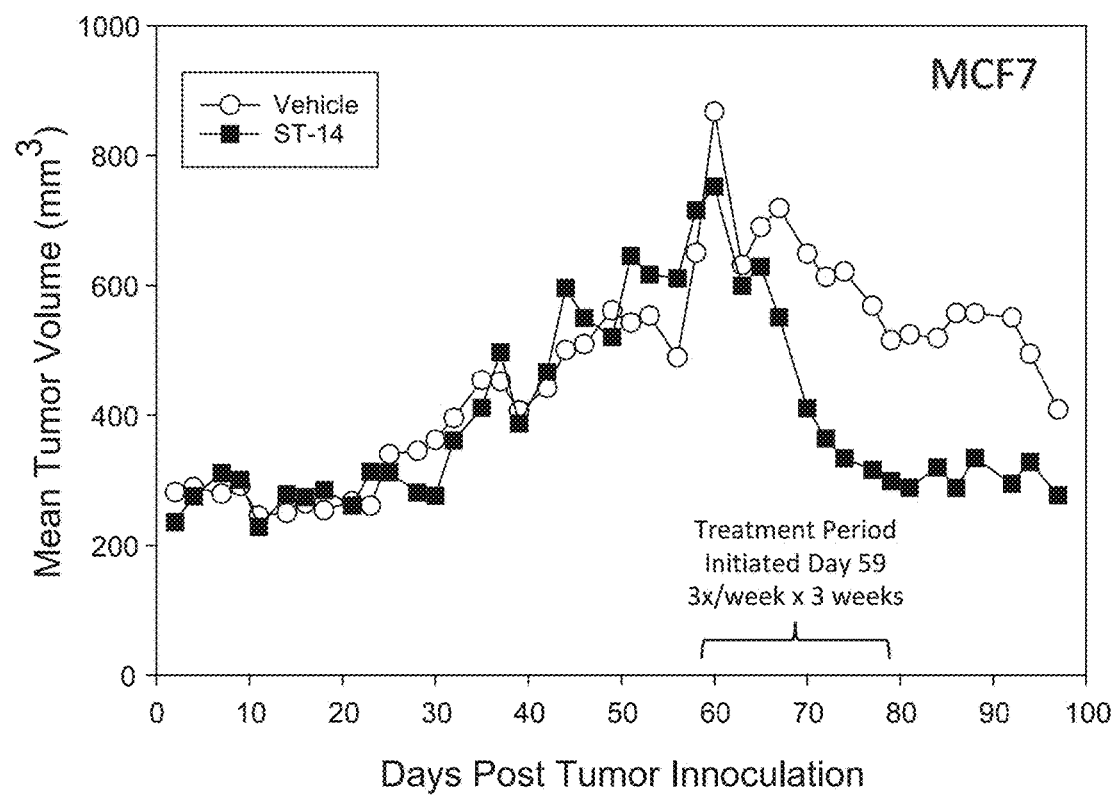

For MCF7 cell tumors, we examined the effect of immediate dosing and delayed dosing. In the immediate dosing experiment, dosing was initiated on day 2 post tumor inoculation (2×10$^6$ cells), with average tumor volume of about 280-330 mm$^3$. ST-14 was administered at a dose of 25 mg/kg via SC injection three times per week for three weeks. In the delayed dosing experiment, dosing was initiated on day 59 post tumor inoculation (vehicle: 2×10$^6$ cells; treatment group: 5×10$^6$ cells). Tumor volume was monitored for 92 days post-inoculation. In both the immediate and delayed treatment groups, ST-14 significantly reduced tumor volume relative to vehicle for the duration of monitoring (FIGS. 11A-11B).

Figure 12:
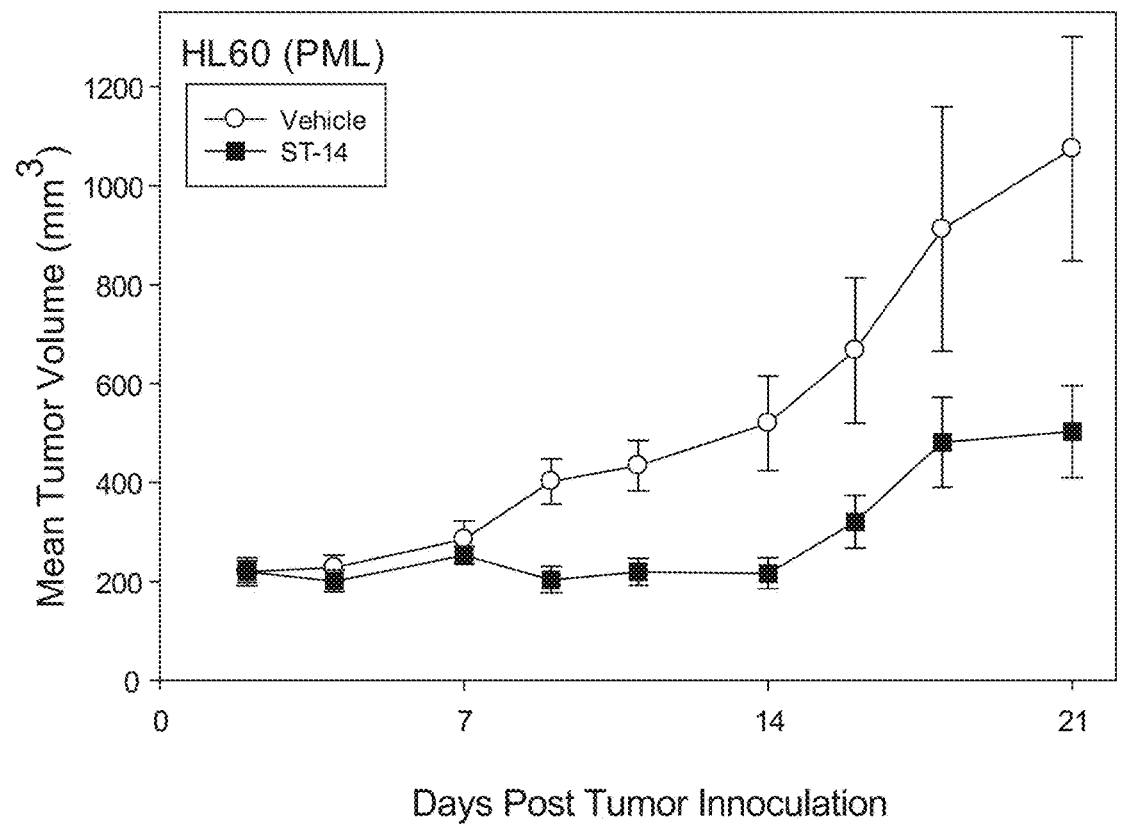
FIG. 12 shows anti-tumor activity of ST-14 in an HL60 subcutaneous tumor model. Nu/J mice were treated with 20 mg/kg SC three times per week for three weeks. Average starting tumor volume was about 220 mm³. Data points represent mean±SEM; p<0.05.

For HL60 cell tumors, dosing was initiated on day 2 post tumor inoculation, with average tumor volume of about 220 mm$^3$. ST-14 was administered at a dose of 20 mg/kg via SC injection three times per week for three weeks. ST-14 significantly reduced tumor volume relative to vehicle (FIG. 12).

Figure 13:
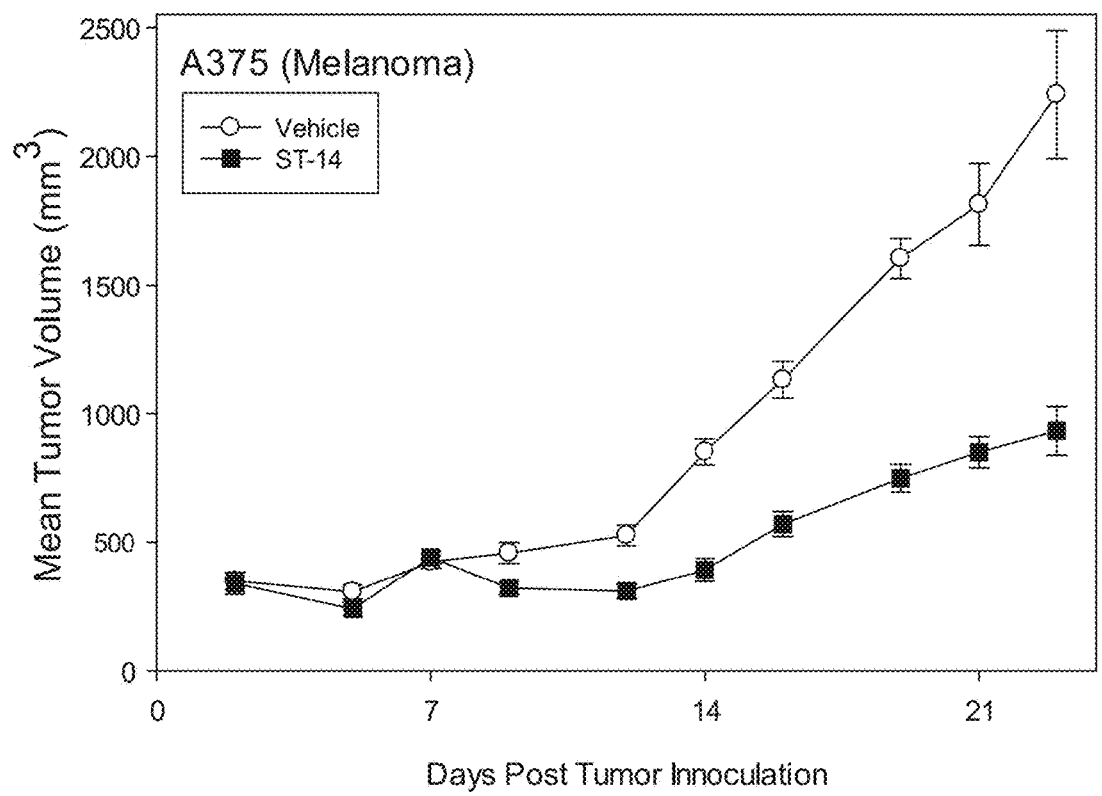
FIG. 13 shows anti-tumor activity of ST-14 in a A375 subcutaneous tumor model. NOD/SCID mice were treated with 25 mg/kg SC twice daily for three weeks. Average starting tumor volume was about 250-344 mm³. Data points represent mean±SEM; p=0.002.

For A375 cell tumors, dosing was initiated on day 2 post tumor inoculation, with average tumor volume of about 250-344 mm$^3$. ST-14 was administered at a dose of 25 mg/kg via SC injection twice daily for three weeks. ST-14 significantly reduced tumor volume relative to vehicle (FIG. 13).

REFERENCES

Acharya A, et al. Experimental identification of homodimerizing B-ZIP families in *Homo sapiens*. *J. Struct. Biol.* 155:130-139 (2006).

Alves I D, et al. Membrane interaction and perturbation mechanisms induced by two cationic cell penetrating peptides with distinct charge distribution. *Biochim. Biophys. Acta* 1780:948-959 (2008).

Angelastro J M, et al. Regulated expression of ATF5 is required for the progression of neural progenitor cells to neurons. *J. Neurosci.* 23:4590-4600 (2003).

Arias A, et al. Regulated ATF5 loss-of-function in adult mice blocks formation and causes regression/eradication of gliomas. *Oncogene* 31:739-751 (2012).

Bernal F, et al. Reactivation of the p53 Tumor Suppressor Pathway by a Stapled p53 Peptide. *J. Am. Chem. Soc.* 129:2456-2457 (2007).

Bird G H, et al. Biophysical Determinants for Cellular Uptake of Hydrocarbon-Stapled Peptide Helices. *Nat. Chem. Biol.* 12:845-852 (2017).

Brodsky J L, et al. Translocation of proteins across the endoplasmic reticulum membrane. *Int. Rev. Cyt.* 178:277-328 (1998).

Chaloin L, et al. Conformations of primary amphipathic carrier peptides in membrane mimicking environments. *Biochem.* 36:11179-11187 (1997).

Chaloin L, et al. Design of carrier peptide-oligonucleotide conjugates with rapid membrane translocation and nuclear localization properties. *Biochem. Biophys. Res. Commun.* 243:601-608 (1998).

Chen A, et al. ATF5 is overexpressed in epithelial ovarian carcinomas and interference with its function increases apoptosis through the downregulation of Bcl-2 in SKOV-3 cells. *Int. J. Gynecol. Pathol.* 31:532-537 (2012).

Cruz J, et al. A membrane-translocating peptide penetrates into bilayers without significant bilayer perturbations. *Biophys. J.* 104:2419-2428 (2013).

Derossi D, et al. Trojan peptides: the penetratin system for intracellular delivery. *Trends Cell Biol.* 8:84-87 (1998).

Elliott G, et al. Intercellular trafficking and protein delivery by a Herpesvirus structural protein. *Cell* 88:223-233 (1997).

Elmquist A, et al. VE-cadherin-derived cell-penetrating peptide, pVEC, with carrier functions. *Exp. Cell Res.* 269:237-244 (2001).

Futaki S, et al. Arginine-rich peptides. An abundant source of membrane-permeable peptides having potential as carriers for intracellular protein delivery. *J. Biol. Chem.* 276:5836-5840 (2001).

Gautam A, et al. CPPsite: a curated database of cell penetrating peptides. Database doi:10.1093/database/bas015 (2012).

Greene L A, et al. The transcription factor ATF5: role in neurodevelopment and neural tumors. *J. Neurochem.* 108:11-22 (2009).

Hällbrink M, et al. Cargo delivery kinetics of cell-penetrating peptides. *Biochim. Biophys. Acta* 1515:101-109 (2001).

Heitz F, et al. Twenty years of cell-penetrating peptides: from molecular mechanisms to therapeutics. *Brit. J. Pharmacol.* 157:195-206 (2009).

Hervé F, et al. CNS delivery via adsorptive transcytosis. *AAPS J.* 10:455-472 (2008).

Jo, D, et al. Intracellular protein therapy with SOCS3 inhibits inflammation and apoptosis. *Nat. Med.* 11:892-898 (2005).

Karpel-Massler G, et al. A Synthetic Cell-Penetrating Dominant-Negative ATF5 Peptide Exerts Anticancer Activity against a Broad Spectrum of Treatment-Resistant Cancers. *Clin. Cancer Res.* 22:4698-4711 (2016).

Kilk K, et al. Cellular internalization of a cargo complex with a novel peptide derived from the third helix of the islet-1 homeodomain. Comparison with the penetratin peptide. *Bioconjug. Chem.* 12:911-916 (2001).

Klein J S, et al. Design and characterization of structured protein linkers with differing flexibilities. *Protein Eng. Des. Sel.* 27:325-330 (2014).

Kosugi S, et al. Six Classes of Nuclear Localization Signals Specific to Different Binding Grooves of Importin α. *J. Biol. Chem.* 284:478-485 (2009).

Krautwald S, et al. Inhibition of regulated cell death by cell-penetrating peptides. *Cell. Mol. Life Sci.* 73:2269-2284 (2016).

Krylov D, et al. Extending dimerization interfaces: the bZIP basic region can form a coiled-coil. *EMBO J.* 14:5329-5337 (1995).

Kumar P, et al. Transvascular delivery of small interfering RNA to the central nervous system. *Nature* 448:39-43 (2007).

Kwon S-J, et al. Transduction of the MPG-tagged fusion protein into mammalian cells and oocytes depends on amiloride-sensitive endocytic pathway. *BMC Biotechnol.* 9:73-84 (2009).

Lange A, et al. Classical Nuclear Localization Signals: Definition, Function, and Interaction with Importin α. *J. Biol. Chem.* 282:5101-5105 (2007).

Le Chevalier Isaad A, et al. Side chain-to-side chain cyclization by click reaction. *J. Pept. Sci.* 15:451-454 (2009).

Lindgren M, et al. Cell-penetrating peptides. *Trends Pharmacol. Sci.* 21:99-103 (2000).

Lundberg P, et al. Delivery of short interfering RNA using endosomolytic cell-penetrating peptides. *FASEB J.* 21:2664-2671 (2007).

Magzoub M, et al. Interaction and structure induction of cell-penetrating peptides in the presence of phospholipid vesicles. *Biochim. Biophys. Acta* 1512:77-89 (2001).

Mattaj I W, et al. Nucleocytoplasmic Transport: The Soluble Phase. *Ann. Rev. Biochem.* 67:265-306 (1998).

Mitchell D J, et al. Polyarginine enters cells more efficiently than other polycationic homopolymers. *J. Pept. Res.* 56:318-325 (2000).

Moll J R, et al. Attractive interhelical electrostatic interactions in the proline- and acidic-rich region (PAR) leucine zipper subfamily preclude heterodimerization with other basic leucine zipper subfamilies. *J. Biol. Chem.* 275:34826-34832 (2000).

Monaco S E, et al. The transcription factor ATF5 is widely expressed in carcinomas, and interference with its function selectively kills neoplastic, but not nontransformed, breast cell lines. *Int. J. Cancer* 120:1883-1890 (2007).

Morris M C, et al. A new peptide vector for efficient delivery of oligonucleotides into mammalian cells. *Nucleic Acids Res.* 25:2730-2736 (1997).

Morris M C, et al. A peptide carrier for the delivery of biologically active proteins into mammalian cells. *Nat. Biotechnol.* 19:1173-1176 (2001).

Muñoz-Morris M A et al. The peptide carrier Pep-1 forms biologically efficient nanoparticle complexes. *Biochem. Biophys. Res. Commun.* 355:877-882 (2007).

Munyendo W L L, et al. Cell penetrating peptides in the delivery of biopharmaceuticals. *Biomolecules* 2:187-202 (2012).

Oehlke J, et al. Cellular uptake of an alpha-helical amphipathic model peptide with the potential to deliver polar compounds into the cell interior non-endocytically. *Biochim. Biophys. Acta* 1414:127-139 (1998).

Olive M, et al. A dominant negative activation protein-1 (AP1) that abolishes DNA binding and inhibits oncogenesis. *J. Biol. Chem.* 272:18586-18594 (1997).

Patgiri A, et al. A hydrogen bond surrogate approach for stabilization of short peptide sequences in alpha helical conformation. *Acc. Chem. Res.* 41:1289-1300 (2008).

Pooga M, et al. Cell penetration by transportan. *FASEB J.* 12:67-77 (1998).

Ragin A. D. et al. Cellular Import Mediated by Nuclear Localization Signal Peptide Sequences. *Chemist and Biology.* 8:943-948 (2002).

Rousselle C, et al. Enhanced delivery of doxorubicin into the brain via a peptide-vector-mediated strategy: saturation kinetics and specificity. *J. Pharmacol. Exp. Ther.* 296:124-131 (2001).

Schafmeister C E, et al. An All-Hydrocarbon Cross-Linking System for Enhancing the Helicity and Metabolic Stability of Peptides. *J. Am. Chem. Soc.* 122:5891-5892 (2000).

Scheller A, et al. Structural requirements for cellular uptake of alpha-helical amphipathic peptides. *J. Peptide Sci.* 5:185-194 (1999).

Schmidt M C, et al. Translocation of human calcitonin in respiratory nasal epithelium is associated with self assembly in lipid membrane. *Biochem.* 37:16582-16590 (1998).

Sheng, Z, et al. An activating transcription factor 5-mediated survival pathway as a target for cancer therapy? *Oncotarget.* 1:457-460 (2010a).

Sheng Z, et al. A genome-wide RNA interference screen reveals an essential CREB3L2-ATF5-MCL1 survival pathway in malignant glioma with therapeutic implications. *Nat. Med.* 16:671-677 (2010b).

Soomets U, et al. Deletion analogues of transportan. *Biochim. Biophys Acta* 1467:165-176 (2000).

Suzuki T, et al. Possible existence of common internalization mechanisms among arginine-rich peptides. *J. Biol. Chem.* 277:2437-2443 (2002).

Thorén P E G, et al. The Antennapedia peptide penetratin translocates across lipid bilayers—the first direct observation. *FEBS Lett.* 482:265-68 (2000).

Vivès E, et al. A truncated HIV-1 Tat protein basic domain rapidly translocates through the plasma membrane and accumulates in the cell nucleus. *J. Biol. Chem.* 272:16010-16017 (1997).

Wang X-Y, et al. Synthesis of small cyclic peptides containing the disulfide bond. *ARKIVOC* xi:148-154 (2006).

Wender P A, et al. The design, synthesis, and evaluation of molecules that enable or enhance cellular uptake: peptoid molecular transporters. *Proc. Natl. Acad. Sci. U.S.A.* 97:13003-13008 (2000).

Zhao Y, et al. Chemical engineering of cell penetrating antibodies. *J. Immunol. Methods* 254:137-45 (2001).

Zou L L, et al. Cell-penetrating peptide-mediated therapeutic molecule delivery into the central nervous system. *Curr. Neuropharmacol.* 11:197-208 (2013).

The present invention is further described by the following claims.

The invention claimed is:

1. An activating transcription factor 5 (ATF5) peptide comprising a truncated ATF5 leucine zipper region, wherein the truncated ATF5 leucine zipper region has a D-amino acid sequence VAEAREELERLEARLGQARGEL (SEQ ID NO: 65).

2. The ATF5 peptide according to claim 1 comprising a D-amino acid sequence (SEQ ID NO: 14)
VAEAREELERLEARLGQARGELKKWKMRRNQFWLKLQR, wherein the ATF5 peptide is a cell-penetrating peptide.

3. The ATF5 peptide according to claim 1, wherein the peptide does not comprise an extended leucine zipper region.

4. The ATF5 peptide according to claim 1, wherein the peptide comprises an N-terminal acetyl group and/or a C-terminal amide group.

5. A composition comprising the ATF5 peptide according to claim 1.

6. The composition according to claim 5, which is a pharmaceutical composition.

7. A kit comprising the ATF5 peptide according to claim 1.

8. A method of promoting cytotoxicity in a neoplastic cell, the method comprising contacting the neoplastic cell with the ATF5 peptide according to claim 1.

9. A method of inhibiting proliferation of a neoplastic cell, the method comprising contacting the neoplastic cell with the ATF5 peptide according to claim 1.

* * * * *